US006429010B1

(12) United States Patent
Greengard et al.

(10) Patent No.: US 6,429,010 B1
(45) Date of Patent: *Aug. 6, 2002

(54) DNA ENCODING THE HUMAN SYNAPSIN III GENE AND USES THEREOF

(75) Inventors: Paul Greengard; Barbara Porton; Hung-Teh Kao, all of New York, NY (US)

(73) Assignee: The Rockefeller University, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/129,668

(22) Filed: Aug. 5, 1998

Related U.S. Application Data

(63) Continuation-in-part of application No. 08/906,865, filed on Aug. 6, 1997, now Pat. No. 6,040,168.

(51) Int. Cl.[7] ............... C12N 15/00; C12N 5/00; C07H 21/04
(52) U.S. Cl. ............... 435/320.1; 435/252.31; 435/252.33; 435/252.34; 435/252.35; 435/254.11; 435/254.2; 435/325; 435/348; 435/352; 435/358; 435/362; 435/366; 435/368; 435/419; 536/23.5
(58) Field of Search .................. 536/23.1, 23.5, 536/24.31; 435/69.1, 69.3, 300.1, 325, 358, 362, 366, 348, 352, 368, 419, 252.31–252.35, 254.11, 254.2, 252.3

(56) References Cited

PUBLICATIONS

Burgess et al., The Journal of Cell Biology 111:2129–2138, 1990.*

Lazar et al. Cellular and Molecular Biology, 8(3):1247–1252, Mar. 1988.*

Stryer, "Biochemistry", 1951 W H. Freeman & Company San Francisco CA pp. 512–513.*

Siow et al, Biochemistry, 31:4268–4275, 1992.*

ATCC Catalogue of Cell Lines & Hybridomas, 7th Ed., 1992 pp. 73, 74, 213, 214, 269.*

Lebo et al. Cold Spring Harbor Symposia on Quantitative Biology, 1986 vol. LI pp. 169–176.*

Genbank 99, Accession Z71183, Apr. 17, 1996.*

Kao et al PNAS, 95(8):4667–4672, 1998.*

* cited by examiner

*Primary Examiner*—Patricia A. Duffy
(74) *Attorney, Agent, or Firm*—Klauber & Jackson

(57) ABSTRACT

A new synapsin protein, designated synapsin III, its amino acid sequence, and its human gene have been isolated and characterized. Furthermore, isoforms of synapsin III, e.g., synapsin IIIa, IIIb and IIIc, and have isolated and characterized, and cDNA encoding these isoforms has also been isolated and characterized. The synapsin III gene is located on human chromosome 22, in the vicinity of a region previously identified as a susceptibility locus for schizophrenia. The information and experimental tools provided by this discovery can be used to generate new therapeutic agents or diagnostic assays for this new protein, its associated mRNA or its associated genomic DNA. Due to its role in neurotransmission and synaptogenesis, isoforms of synapsin III are associated with the symptoms of psychiatric diseases, especially schizophrenia.

8 Claims, 20 Drawing Sheets

FIG. 4A

```
TGG GTA GGA GCC AGT CAT CTC CAT CCA ACA GCC ATG AAT TTC CTC CGG CGA CGT CTC   60
 W   V   G   A   S   H   L   H   P   T   A   M   N   F   L   R   R   R   L

TCT GAC AGC AGC TTC ATG GCC AAC CTG CCT AAT GGC TAT ATG ACG GAC CTG CAA CGC CCA  120
 S   D   S   S   F   M   A   N   L   P   N   G   Y   M   T   D   L   Q   R   P

GAT AGC TCC ACC AGC TCA CCT GCT TCC CCC GCC ATG GAG AGG CAC CCC CAG CCC CTG  180
 D   S   S   T   S   S   P   A   S   P   A   M   E   R   H   P   Q   P   L

GCT GCC TCC TTC TCC TCT CCA GGA TCC AGC CTT TTT AGC CTC TCC AGT GCC ATG AAG  240
 A   A   S   F   S   S   P   G   S   S   L   F   S   L   S   S   A   M   K

CAG GCC CCT CAG GCC ACC TCA GGA ATG GAG ATG GAG CCT CCA GGT CCC TCC ACG CCC ATT GTT  300
 Q   A   P   Q   A   T   S   G   M   E   M   E   P   P   G   P   S   T   P   I   V

CAA AGA CCC AGG ATC CTG TTG GTG ATC GAT GAT GCC CAT ACA GAC TGG TCG AAG TAT TTC  360
 Q   R   P   R   I   L   L   V   I   D   D   A   H   T   D   W   S   K   Y   F

CAT GGG AAG AAG GTG AAT GGA GAG ATT GAG ATC CGA GTG GAG CAG GCT GAA TTC TCA GAG  420
 H   G   K   K   V   N   G   E   I   E   I   R   V   E   Q   A   E   F   S   E

TTG AAC CTA GCT GCC TAT GTG ACC GGG GGC TGC ATG GTG GAC ATG CAG GTC GTG AGA AAT  480
 L   N   L   A   A   Y   V   T   G   G   C   M   V   D   M   Q   V   V   R   N

GGG ACC AAA GTG GTG AGC AGA TCC TTC AAG CCA GAC TTC ATC CTG GTC CGC CAG CAT GCC  540
 G   T   K   V   V   S   R   S   F   K   P   D   F   I   L   V   R   Q   H   A

TAC AGC ATG GCC CTG GGG GAA GAC TAC CGC AGC ATC GGC CTG CAG TAT GGA GGG  600
 Y   S   M   A   L   G   E   D   Y   R   S   I   G   L   Q   Y   G   G
```

FIG. 4B

```
CTG CCT GCT GTC AAC TCT CTC TAC TCC GTC TAC AAC TTC TGC AGC AAG CCC TGG GTG TTC    660
 L   P   A   V   N   S   L   Y   S   V   Y   N   F   C   S   K   P   W   V   F

TCT CAG CTC ATT AAG ATC TTC CAT TCC CTG GGT CCT GAG AAG TTC CCG CTT GTG GAG CAA    720
 S   Q   L   I   K   I   F   H   S   L   G   P   E   K   F   P   L   V   E   Q

ACA TTT TTC CCC AAC CAT AAG CCA ATG GTC ACA GCC CCA CAC TTC CCG GTA GTC AAG        780
 T   F   F   P   N   H   K   P   M   V   T   A   P   H   F   P   V   V   K

CTG GGA CAT GCC CAC GCT GGA ATG AAG GGA ATC AAA GTG GAA AAC CAG CTT GAC TTC CAG    840
 L   G   H   A   H   A   G   M   K   G   I   K   V   E   N   Q   L   D   F   Q

GAC ATC ACC AGC GTG GTC GCC ATG CGC ATC CAG AAA ACA TAC GCC ACC GAG GCG TTC ATC GAC 900
 D   I   T   S   V   V   A   M   R   I   Q   K   T   Y   A   T   E   A   F   I   D

TCC AAG TAC GAC ATC TCT GGG AAC TGG AAG TAC AAC TAC ATG AAG GCT TAC ATG AGA ACC    960
 S   K   Y   D   I   S   G   N   W   K   Y   N   Y   M   K   A   Y   M   R   T

TCC ATC TCT GGG AAC TGG AAG CTG TGG GAC AGC TGC TCG GAA ATG CTG GAG CAG GTG GCC ATG 1020
 S   I   S   G   N   W   K   L   W   D   S   C   S   E   M   L   E   Q   V   A   M

ACA GAG AGG TAC AGG CTG TGG GAC AGC TGC TCG GAA ATG TTT GGC GGC CTG GAC ATC        1080
 T   E   R   Y   R   L   W   D   S   C   S   E   M   F   G   G   L   D   I

TGT GCC GTC AAG GCT GTC CAC AGC AAG GAT GGC AGA GAT TAC ATC ATC GAG GTA ATG GAC    1140
 C   A   V   K   A   V   H   S   K   D   G   R   D   Y   I   I   E   V   M   D
```

FIG.4C

```
AGC TCA ATG CCG CTG ATT GGA GAG CAT GTG GAA GAG GAC AGA CAG CTG ATG GCC GAC CTT   1200
 S   S   M   P   L   I   G   E   H   V   E   E   D   R   Q   L   M   A   D   L

GTT GTC TCC AAA ATG AGC CAG CTC CCG ATG CCA GGA GGC ACA GCG CCC TCC CCC CTC AGA   1260
 V   V   S   K   M   S   Q   L   P   M   P   G   G   T   A   P   S   P   L   R

CCT TGG GCT CCA CAG ATT AAA TCA GCG AAA TCC CCA GGG CAA GCC CAG CTG GGG CCT CAG   1320
 P   W   A   P   Q   I   K   S   A   K   S   P   G   Q   A   Q   L   G   P   Q

CTA RGC CAG CCC CAG AGA TCT GGA AGC CCT CCG CAA GGC CCT CGC CAA GCT CAG TCT CCT   1380
 L   X   Q   P   Q   R   S   G   S   P   P   Q   G   P   R   Q   A   Q   S   P

CAG CCC CAG TCC CAG TCC GGA TCT CCA CAG CAG AGG CTC TCC CCA CAA GGC CAG CAG CCC   1440
 Q   P   Q   S   Q   S   G   S   P   Q   Q   R   L   S   P   Q   G   Q   Q   P

CTG AGC CCC CAG AGC AGC TCC GGA TCT CCA CAG CAG AGG TCA CCA AGG CCA GGT CAG CTA TCC   1500
 L   S   P   Q   S   S   S   G   S   P   Q   Q   R   S   P   R   P   G   Q   L   S

CGG GCA TCC AGT GGC CCT GTG CAG GGC CGT AGT ACC TCC CAG GCC TCC AAG CCA ACC CTC GCC TCA   1560
 R   A   S   S   G   P   V   Q   G   R   S   T   S   Q   A   S   K   P   T   L   A   S

CAG CCC CGG CCC CCT CAG GGC CAG AAC CAR GCC GGG CGT AGT ACC TCC CAG GGT GAA GAG TCC AAG AAG   1620
 Q   P   R   P   P   Q   G   Q   N   Q   A   G   R   S   T   S   Q   G   E   E   S   K   K

CCA GCA CCA CCC CGG CAT CTC AAC AGC CTG ACT AAA TCT CAG TCC CTG AAC AGC CTC AGC ACA   1680
 P   A   P   P   R   H   L   N   S   L   T   K   S   Q   S   L   N   S   L   S   T
```

FIG.4D

```
TCC GAC ACC TCC CAG CGT GGG ACC CCA AGT GAA GAC GAG GCC AAG GCT GAA ACC ATC CGC    1740
 S   D   T   S   Q   R   G   T   P   S   E   D   E   A   K   A   E   T   I   R

AAC CTG AGG AAG TCT TTT GCC AGC CTG TTC TCT GAC TAA CGC CAT CCA GGC TGG GAG GGG    1800
 N   L   R   K   S   F   A   S   L   F   S   D   .

AAG AGT GCT ATG GTA CAC TCG TCC CCY TCC TGC CTC ATC TTC CTT CTC AGC CTT GGT TCC    1860

TGA TGG GAA CAG AAT GGA GGG CCT GAG AAC ATA CTT TCT AAA TGC CTT TGA CCC AGG AAC    1920

CGA TTA TCT ATA TTT GTT CCC ATT TTC CTT CAC CGT GAC ATT CCA GCA TTG TCT GAC TGT    1980

GAG GTG GGC CTT TGA GAG CCT CCA GGT TCC TCA AAA CAG GCC TGA GCG ATG GGC ATC ACA    2040

CCC TCT GCC TAC CCA CGT GCA TGC TTA CCT GCC AGA TAA CCA AGT GAG ATG TCT GCG AGT    2100

GGC TAG TTT TCA CAT TCT TAC TAG TGT TTG GCT CAC CTT TGG GCA AAG GCC CCY TTA GGC    2160

CTT GCC CCA CCT CCA TCA AAC GCA GAC ACT GTA GTC AGA CCT CAG CAA TAT AGG AGG CAA    2220

TAA TCT TTT AAC AGT GTT TTG CAA ACA AAC AAA AAA AAA AAA AAA AA
```

FIG.5A

```
Ia     -MNYLRRRLS DSNFMANLPN GYMTDLQRPQ PPPPP---- GAHSPGATPG    45
IIa    -MNFLRRRLS DSSFIANLPN GYMTDLQRPE PQQPPPPPP GPGAASASAA    50
IIIa   -MNFLRRRLS DSSFMANLPN GYMTDLQRPD --------- ----SSTSS    34

Ia     PGTATAERSS GVAPAASPAA -PSPGSSGGG GFFSSLSNAV KQTTAAAAAT    94
IIa    PPTASPGPER RPPPASAPAA QPAPTPSVGS SFFSSLSQAV KQTAASAG--    98
IIIa   PASPAMER-R HPQPLAASF- --SSP----G SLFSSLSSAM KQAPQATS-G    76

Ia     FSEQVGGGSG GAGRGGAASR VLLVIDEPHT DWAKYFKGKK IHGEIDIKVE   144
IIa    LVDAPAPAP- AAAR---KAK VLLVVDEPHA DWAKCFRGKK VLGDYDIKVE   144
IIIa   LMEPPGPSTP IVQR----PR ILLVIDDAHT DWSKYFHGKK VNGEIEIRVE   122

Ia     QAEFSDLNLV AHANGGFSVD MEVLRNGVKV V-RSLKPDFV LIRQHAFSMA   193
IIa    QAEFSELNLV AHADGTYAVD MQVLRNGTKV V-RSFRPDFV LIRQHAFGMA   193
IIIa   QAEFSELNLA AYVTGGCMVD MQVVRNGTKV VSRSFKPDFI LVRQHAYSMA   172

Ia     RNGDYRSLVI GLQYAGIPSV NSLHSVYNFC DKPWVFAQMV RLHKKLGTEE   243
IIa    ENEDFRHLII GMDYAGLPSI NSLESIYNFC DKPWVFAQLV AIYKTLGGEK   243
IIIa   LGEDYRSLVI GLQYGGLPAV NSLYSVYNFC SKPWVFSQLI KIFHSLGPEK   222
```

FIG. 5B

```
Ia    FPLIDQTFYP NHKEML SSTT YPVVVKMGHA HSGMGKYKVD NQHDFQDIAS    293
IIa   FPLIEQTYYP NHKEML TLPT FPVVVKIGHA HSGMGKYKVE NHYDFQDIAS    293
IIIa  FPLVEQTFFP NHKPMVTAPH FPVVVKLGHA HAGMGKIKVE NQLDFQDITS    272

Ia    VVALTKTYAT AEPFIDAKYD VRVQKIGQNY KAYMRTSVSG NMKTNTGSAM    343
IIa   VVALTQTYAT AEPFIDSKYD IRVQKIGQNY KAYMRTSISG NMKTNTGSAM    343
IIIa  VVAMAKTYAT TEAFIDSKYD IRLQKIGSNY KAYMRTSISG NMKANTGSAM    322

Ia    LEQIAMSDRY FGGLDICAVE ALHGKDGRDH IIEVVGSSMP                393
IIa   LEQIAMSDRY FGGLDICAVK AVHGKDGKDY IFEVMDCSMP                393
IIIa  LEQVAMTERY FGGLDICAVK AVHSKDGRDY IIEVMDSSMP                372

Ia    LIGDHQDEDK QLIVELVVNK MAQALPRQRQ RDASPGRGSH GQTSPGALP      443
IIa   LIGEHQVEDR QLITELVISK MNQLLSR--T PALSPQRPLT TQQPQSGTL-     440
IIIa  LIGEHVEEDR QLMADLVVSK MSQL-PMPGG TAPSPLRPWA PQIKSAKSPG     421

Ia    LGRQTSQQPA GPPAQQEPPP QGGPPPQP-GP GPQRQGPPLQ QRPPPQGQQH    492
IIa   ---KDPDSSK TPP--QRPPP QGGPGQP--Q GMQPPGKVL- ---PP---RR    476
IIIa  ---QAQLGPQ LGQPQPRPPP QGGPROAQSP QPQRSGSPSQ QRLSPQGQQP    468
```

FIG.5C

```
Ia   LSGLGPPAGS PLPQRLPSPT SAPQQPASQA APPTQGGQRQ SRPVAGGPGA   542
IIa  L------PPGP SLP-----PS SSSSSSSSSS APQ-------  -RP--GGPTT   506
IIIa LS----PQSGS PQQQR---SPG SPQLSRASSG SSP------- NQA--SKPGA   504

Ia   PPAARPPASP SPQRQAGPPQ ATRQTSVSGP APPKASGAPP GGQQRQGPPQ   592
IIa  ---------- --------- SS--SSLAEA QPPLA-----  ----APPQ   529
IIIa ---------- --------- ----TLASQ PR--PPVQGR STSQQG-----  ---EESK   527

Ia   KPPGPAGPTR QASQAGPVPR TGPPTTQQPR PSGPGPAGAP KPQLAQKPSQ   642
IIa  KP-------- --------- ----QPH---  --------- -PQL-NK-SQ   541
IIIa KP-------- --------- ----APPH--  --------- -PHL-NK-SQ   540

Ia   DVPPPATAAA GGPPHPQLFN LPEPAPPRPS LSQDEVKAET IRSLRKSFAS   692
IIa  SL----TNA- ---------  --FS FSESSFFRSS ANEDEAKAET IRSLRKSFAS   578
IIIa SL----TNS- ---------  --LS TSDTS-QRGT PSEDEAKAET IRNLRKSFAS   576

Ia   LFSD   696
IIa  LFSD   582
IIIa LFSD   580
```

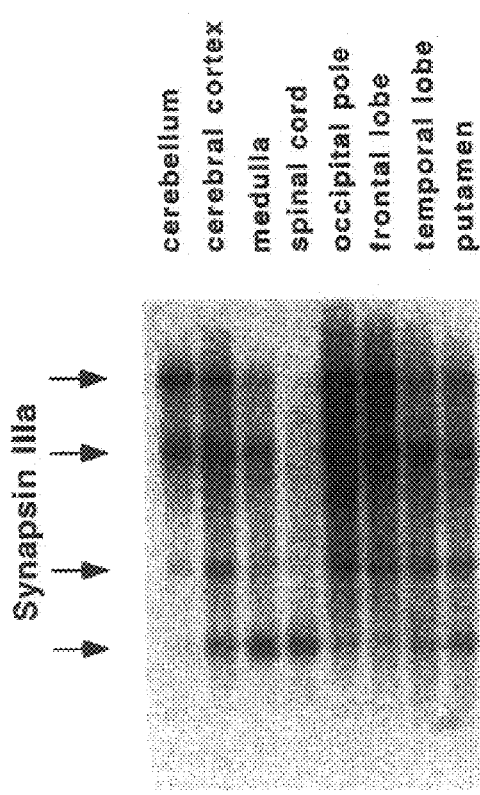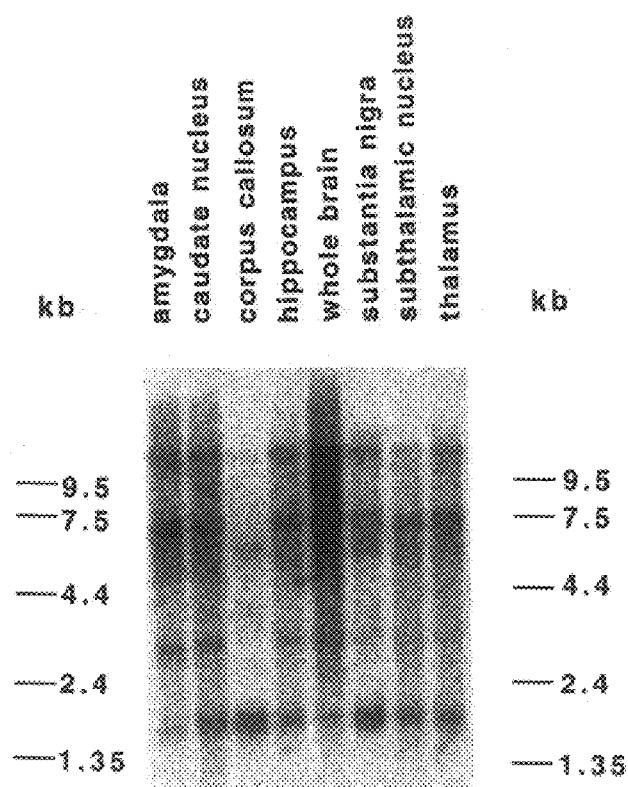

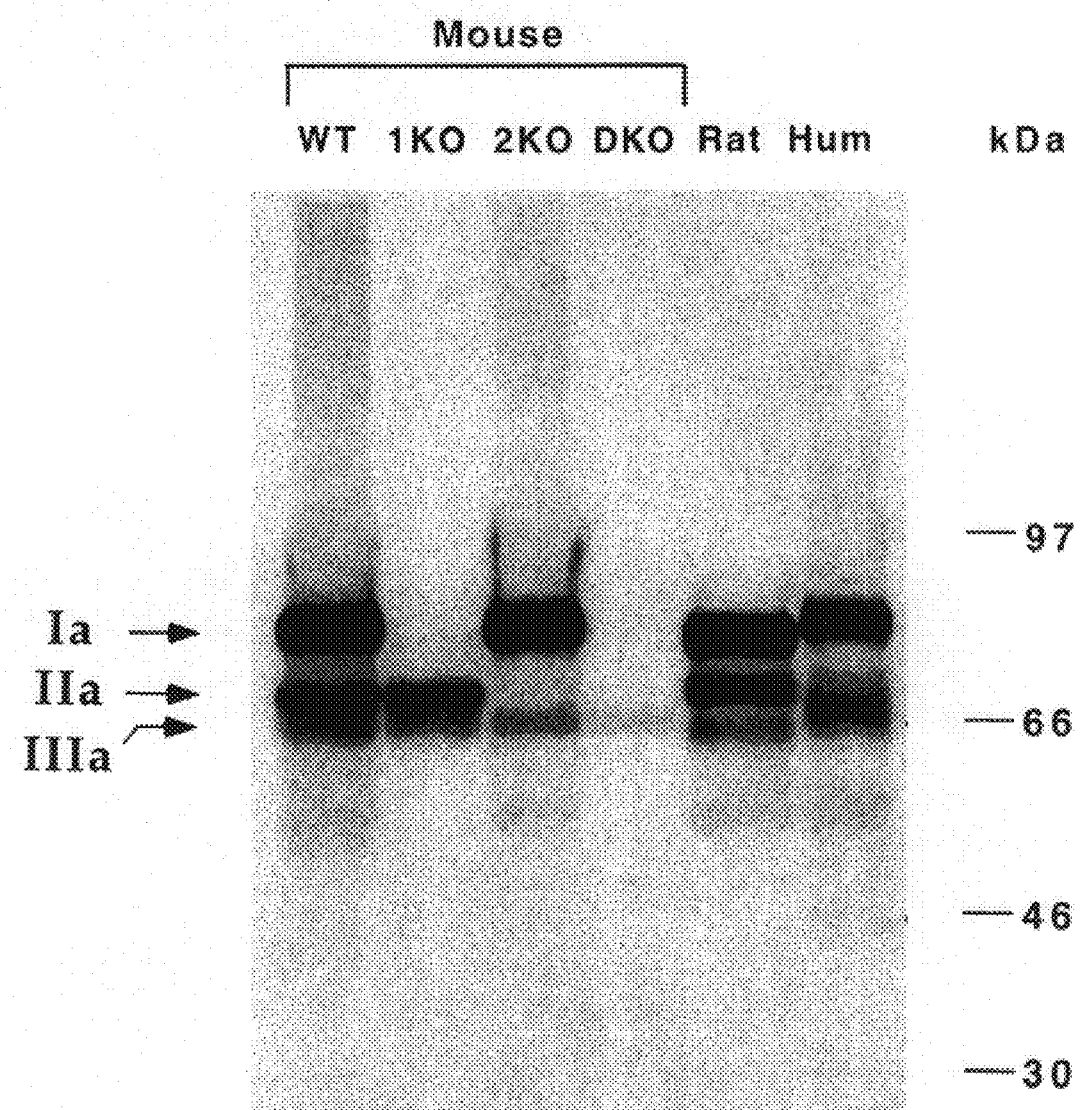

FIG.8

MNFLRRRLSDSSFMANLPNGYMTDLQRPDSSTSSPASPAMERRHPQPLAASFSSPGSSLFSSLSSAMKQAPQATSGLMEP

PGPSTPIVQRPRILLVIDDAHTDWSKYFHGKKVNGEIEIRVEQAEFSELNLAAYVTGGCMVDMQVVRNGTKVVSRSFKPD

FILVRQHAYSMALGEDYRSLVIGLQYGGLPAVNSLYSVYNFCSKPWVFSQLIKIFHSLGPEKFPLVEQTFFPNHKPMVTA

PHFPVVVKLGHAHAGMGKIKVENQLDFQDITSVVAMAKTYATTEAFIDSKYDIRIQKIGSNYKAYMRTSISGNWKANTGS

AMLEQVAMTERYRLWVDSCSEMFGGLDICAVKAVHSKDGRDYIIEVMDSSMPLIGEHVEEDRQLMADLVVSKMSQLPMPG

GTAPSPLRPWEALAKLSLLSPRDLEAPPNRGSPHKASSP

FIG.9A

TGGGTAGGAGCCAGTCATCTCCATCCACAGCCATGAATTCCTCCGGCGACGTCTCTCTGACAGCAGCTTCATGGC

CAACCTGCCTAATGGCTATATGACGGACCTGCAACGCCCAGATAGCTCCACCAGCTCACCTGCTTCCCCGCCATGGAGA

GGAGGCACCCCCAGCCCCTGGCTGCCTCCTTCTCTCCAGGATCCAGCCTTTTTAGCTCCCTCTCCAGTGCCATGAAG

CAGGCCCCTCAGGCCACCTCAGGACTGATGGAGCCTCCAGGTCCCTCCACGCCCATTGTTCAAAGACCCAGGATCCTGTT

GGTGATCGATGATGCCCATACAGACTGGTCGAAGTATTTCCATGGGAAGAAGGTGAATGGAGAGATTGAGATCCGAGTGG

AGCAGGCTGAATTCTCAGAGTTGAACCTAGCTGCCTATGTGACCGGGGGCTGCATGGTGGACATGCAGGTCGTGAGAAAT

GGGACCAAAGTGGTGAGCAGATCCTTCAAGCCAGACTTCATCCTGGTCCGCCAGCATGCCTACAGCATGGCCCTGGGGGA

AGACTACCGCAGCCTGGTCATCGGCCTGCAGTATGGAGGGCTGCCTGCTGTCAACTCTCTCTACTCCGTCTACAACTTCT

GCAGCAAGCCCCTGGGTGTTCTCTCAGCTCATTAAGATCTTCCATTCCCTGGGTCCTGAGAAGTTCCCGCTTGTGGAGCAA

ACATTTTTCCCAACCATAAGCCAATGGTCACAGCCCCACACTTCCCGGTGGTAGTCAAGCTGGGACATGCCCACGCTGG

AATGGAAAGATCAAAGTGGAAAACCAGCTTGACTTCCAGGACATCCGCATCCAGAAAATTGGATCCAACTACAAGGCTTACATGAGAACC

CCACCGAGGCGTTCATCGACTCCAAGTACGACATCGCCATGGTCGCCATGGCCAAAACATACGCCA

TCCATCTCTGGGAACTGGAAGGCCAACACAGGCTCTGCCATGCTGACAGAGAGGTACAGGCTGTG

FIG.9B

```
GGTGGACAGCTGCTCTCGGAAATGTTTGGGCCTGGACATCTGTGCCGTCAAGGCTGTCCACAGCAAGGATGGCAGAGATT
ACATCATCGAGGTAATGGACAGCTTCAATGCCGCTGATTGGAAGAGACATGTGGAAGAGACAGACAGCTGATGGCCGACCTT
GTTGTCTCCAAAATGAGCCAGCTCCCGATGCCAGGAGGCACAGCGGCCCCTCCCCCCTCAGACCCTTGGGAGGCCCTCGCCAA
GCTCAGTCTCCTCAGCCCCAGAGATCTGGAAGCCCCTCCCAACAGAGGCTCTCCCCACAAGGCCAGCAGCCCCTGAGCCC
CCAGTCCGGATCTCCACAGCAGCAAAGGTCACCAGCCTCACCCCGGCATCCAGTGGCAGCTCCCAGCAGGTCCCCAAACC
AGGCCTCCAAGCCAGGTGCCACCCTCGCCTCACAGCCCCTGTGCAGGGCGTAGTACCTCCCAGCAGCACATCCGACAC
GAGTCCAAGAAGCCAGCACCACCCCAAGTGAAGACGAGGCCAAGGCTGAAACCATCCGCAACCTGAGGAAGTCTTTGCCAGCCTGT
CTCCCAGCGTGGGACCCATCCAGGCTGGGAACAGAATGAGGGCCTGAGAACATACTTTCTAAATGCCTTTGACCCCAGGAACCGATTATC
TCTCTGACTAACGCCATCCAGGCTGGGAACAGAATGAGGGCCTGAGAACATACTTTCTAAATGCCTTTGACCCCAGGAACCGATTATC
AGCCTTGGTTCCTGATGGGAACAGAATGAGGGCCTGAGAACATACTTTCTAAATGCCTTTGACCCCAGGAACCGATTATC
TATATTTGTTTCCCATTTTCCTTCACCGTGACATTCCAGCATTGTCTGACTGTGAGGTGGGCCTTTGAGAGCCTCCAGGTT
CCTCAAAACAGGCCTGAGCGATGGGCATCACACCCTCTGCCTACCCACGTGCATGCTTACCTGCCAGATAACCAAGTGAG
ATGTCTGCGAGTGGCTAGTTTTCACATTCTTTACTAGTGTTTGGCTCACCTTTGGGCAAAGGCCCC
```

FIG. 10

MNFLRRRLSDSSFMANLPNGYMTDLQRPDSSTSSPASPAMERRHPQPLAASFSSPGSSLFSSLSSAMKQAPQATSGLMEP
PGPSTPIVQRPRILLVIDDAHTDWSKYFHGKKVNGEIEIRVEQAEFSELNLAAYVTGGCMVDMQVVRNGTKVVSRSFKPD
FILVRQHAYSMALGEDYRSLVIGLQYGGLPAVNSLYSVYNFCSKPWVFSQLIKIFHSLGPEKFPLVEQTFFPNHKPMVTA
PHFPVVVKLGHAHAGMGKIKVENQLDFQDITSVVAMAKTYATTEAFIDSKYDIRIQKIGSNYKAYMRTSISGNWKANTGS
AMLEQVAMTERYRLWVDSCSEMFGGLDICAVKAVHSKDGRDYIIEVMDSSMPLIGEHVEEDRQLMADLVVSKMSQLPMPG
GTAPSPLRPWAPQIKSAKSPGQAQLGPQLGQPQRPPPQANLSP

FIG. 11A

```
TGGGTAGGAGCCAGTCATCTCCATCCATCCACAGCCATGAATTCCTCCGGGACGTCTCTGACAGCAGCTTCATGGC
CAACCTGCCTAATGGCTATATGACGGACCTGCCTCCTTCTCCAGGATCCAGATAGCTCCACCAGCTCACCTGCTTCCCCGCATGGAGA
GGAGGCACCCCAGCCCCCTGGCTGCCTCCTTCTCCAGGACTGATGGAGCCTCCAGGTCCCTCCACGCCCATTGTTCAAAGACCCAGCCTTTTTAGCTCCCTCTCCAGTGCCATGAAG
CAGGCCCCTCAGGCCACCTCAGGACCCATACAGACTGGTCGAAGTATTTCCAGGTCGAAGTATTTCCACGCCCATTGTTCAAAGACCCAGGATCCGAGTCCTGTT
GGTGATCGATGATGCCCTAGCTGAACCTAGCTGCCTATGTGACCGGGGCTGCATGGTGGACATGCAGGTCGTGAGAAAT
AGCAGGCTGAATTCTCAGAGTTGAACCTAGCTGCCTTCAAGCCAGACTTCATCCTGGTCCGCCAGCATGCCTACAGCATGGCCCTGGGGGA
GGGACCAAAGTGGTGAGCAGATCCTTCAAGCCAGACTTCATCCTGGTCCGCCAGCATGCCTACAGCATGGCCCTGGGGGA
AGACTACCGCAGCCTGGTCATCGGCCTGTCTCAGCTCATTAAGATCTTCACAGCCCCACACTTCCCGGTCAGTCAAGCTGGACATGCCCACGCTGG
GCAGCAAGCCCTGGGTGTTCTCTCAGCTCATTAAGATCTTCACAGCCCCACACTTCCCGGTCAGTCAAGCTGGACATGCCCACGCTGG
ACATTTTCCCAACCATAAGCCAATGGTCACAGCCTTGACTTCCAGGACATCACCAGCGTGGTCGCCATGGCCAAAACATACGCCA
AATGGGAAAGATCAAAGTGGAAAACCAGCTTGACTTCCAGGACATCACCAGCGTGGTCGCCATGGCCAAAACATACGCCA
CCACCGAGGCGTTCATCGACTCCAAGTACGACATCCGCTACGACATCCAGAAAATTGGATCCATCCAACTACAAGGCTTACATGAGAACC
```

FIG. 11B

```
TCCATCTCTGGGAACTGGAAGGCCAACACAGGCTCTGCCATGCTGTGGAGCAGGTGGCCATGACAGAGAGGTACAGGCTGTG
GGTGGACAGCTGCTCGGAAATGTTTGGCGGCCTGGACATCTGTGCCGTCAAGGCTGTCCACAGCAAGGATGGCAGAGATT
ACATCATCGAGGTAATGGACAGCTCAATGCCGCTGATTGGAAGAGCATGTGGAAGAGGACAGACAGCTGATGGCCGACCTT
GTTGTCTCCAAAATGAGCCAGCTCCCGATGCCAGGAGGCACAGCCCCTCCCCCTCAGACCCTTGGGCTCCACAGATTAA
ATCAGGGAAATCCCCAGGGCAAGCCTCAGCACATCCGACACCTCCCAGCGTGGGACCCCAAGTGAAGACGAGGCCAAGGCTGAAA
TCAGTCCCTGACTAACGCCTGAGGAGTCTTTTGCCAGCCTCATCTTCCTTCTCAGCCTTGGTTCCTGATGGGAACAGAATGGAGGGCCTGAGAACAT
CCATCCGCAACCTGAGGAGTCTTTTGCCAGCCTCATCTTCCTTCTCAGCCTTGGTTCCTGATGGGAACAGAATGGAGGGCCTGAGAACAT
GTACACTCGTCCCCCTCCCCTCCATCTTCCTTCTCAGCCTTGGTTCCTGATTATCTATATTGTTCCCATTTTCCTTCACCGTGACATTCCAGCATTGT
ACTTTCTAAAATGCCTTTGACCCAGGAACCGATTATCTATATTGTTCCCATTTTCCTTCACCGTGACATTCCAGCATTGT
CTGACTGTGAGGTGGGCCTTTGAGAGCCTCCAGGTTCCTCAAAACAGGCCTGAGGCGATGGGCATCACACCCTCTGCCTAC
CCACGTGCATGCTTACCTGCCAGATAACCAAGTGAGATGTCTGCGGAGTGGCTAGTTTTCACATTCTTACTAGTGTTTGGC
TCACCTTTGGGCAAAGGCCCC
```

DNA ENCODING THE HUMAN SYNAPSIN III GENE AND USES THEREOF

CROSS REFERENCE TO RELATED APPLICATIONS

This Application is a Continuation In Part of application Ser. No. 08/906,865 filed on Aug. 6, 1997 now U.S. Pat. No. 6,040,168, which is hereby incorporated by reference in its entirety.

The research leading to the present invention was supported in part by National Institutes of Mental Health Grant No. MH39327. The Government may have certain rights therein.

TECHNICAL FIELD OF THE INVENTION

The present invention relates generally isoforms of synapsin III, e.g., synapsin IIIa, IIIb, and IIIc. mRNA produced from transcription of the synapsin III gene undergoes alternative splicing and encodes the isoforms. Furthermore, the invention relates to uses of isoforms of synapsin III, and nucleic acids which encode these isoforms, especially in the diagnosis and treatment of schizophrenia.

BACKGROUND OF THE INVENTION

The synapsins are a family of proteins that play a crucial role in the regulation of neurotransmission and in neurodevelopment. Single genes encode synapsins I and II. The synapsin I gene gives rise to two alternatively spliced mRNAs, which in turn, give rise to the synapsin Ia and Ib protein. The synapsin II gene gives rise to two alternatively spliced mRNAs, which in turn, give rise to the synapsin IIa and IIb protein (1).

The synapsin Ia, Ib, IIa, and IIb proteins are all found in the brain, where they are specifically localized to the presynaptic region of neurons, and coat synaptic vesicles. There is considerable experimental evidence that synapsins regulate the release of neurotransmission by becoming phosphorylated through the action of specific protein kinases (2).

There is also compelling evidence from several biological systems that synapsins play a critical role in axonal outgrowth, synapse formation, and synapse maintenance (3–8). Synapsins are potent stimulators of synapse formation, and may be useful as therapeutic agents for neurodegenerative diseases.

To date, no satisfactory candidate susceptibility gene for schizophrenia has been identified within the region of 22q 12–13 human chromosome 22, although several studies report that this region has a statistically significant chance of containing such a gene. Since synapsins play an integral role in neurotransmitter release and synaptogenesis, mutations in the gene therefor could explain many of the defects observed in neurotransmission and in synapse formation in schizophrenia.

Schizophrenia is a psychiatric illness that affects approximately 1% of the population worldwide. The illness is characterized by positive symptoms such as hallucinations, delusions, bizarre behavior, and thought disorder, as well as negative symptoms such as lack of motivation, social withdrawal, and apathy. Unfortunately, there is no objective laboratory test for schizophrenia, and the diagnosis is made by clinical interview. Current medication is effective for treating the positive symptoms of the disease, with little effect on the negative symptoms. Although the cause of schizophrenia is unknown, the disease has a strong genetic component. Research into the genetics of schizophrenia reveals that this disease is heterogeneous and is a "complex genetic" disease—that is, several genes may be involved in the etiology of this disease. In identical twin studies, where one twin is affected by the disease, the other twin has a 50% chance of succumbing to the disease. Since identical twins possess identical genes, the penetrance of the disease in the setting of mutated genes is only 50%. Thus, an unknown environmental component as well as the presence of specific mutated genes, is required for the generation of schizophrenia.

Biochemical and cytological studies suggest that in schizophrenia, defects in neurotransmission and synapses occur. Abnormal neurotransmission affecting the dopamine, serotonin, glutamine, γ-aminobutyric acid, and cholecystokinin systems have been reported in schizophrenia (18). Neurodevelopmental abnormalities are also strongly implicated in schizophrenia, with reports of defects in neuronal cytoskeleton (19), neuronal cytoarchitecture and migration (20), cellular polarity (21), and synaptic pruning (22). Thus, in schizophrenia, at least two processes appear to be aberrant: neurotransmission and neuronal development, primarily affecting the later stages of synapse formation.

These studies indicate that a candidate susceptibility gene for schizophrenia should be expressed in the brain, and would likely play a role in synapse formation and neurotransmission. Furthermore, a candidate susceptibility gene should be genetically linked to schizophrenia. As indicated before, several research groups have independently identified a region on chromosome 22 that appears to possess a candidate susceptibility gene for schizophrenia (9–17). To date, a susceptibility gene has not been identified in this region.

Schizophrenia is a common disease, with a world-wide prevalence of 1%, affecting families of all races and socioeconomic groups, and consuming a significant portion of all medical and social expenses.

Since there is a continuing need for new therapies for such diseases, efforts have been devoted to the characterization and elucidation of the genes for synapsins, and their various attendant uses. The susceptibility gene for schizophrenia has great commercial value both as a diagnostic reagent and for developing new treatments for this disease.

SUMMARY OF THE INVENTION

In accordance with the present invention, novel human cDNAs which encode isoforms of synapsin III, e.g., synapsin IIIa, IIIb, and IIIc have been cloned and characterized. These cDNAs are produced from alternative splicing of RNA complementary to the synapsin III gene, the newest member and third gene of the synapsin family of neuronal phosphoproteins.

This invention thus provides cDNAs of isolated clones that encode the heretofore unknown isoforms of the synapsin III protein, and which can be used to obtain genomic DNA, cDNA or RNA complementary to an isolated clone of the invention. Isolated clones of the invention can be used to isolate mRNA or genomic DNA from human, mammalian or other animal sources, or to isolate related cDNA or genomic clones by the screening of cDNA or genomic libraries. Furthermore, the clones themselves, or fragments derived from the clones, can be inserted in suitable vectors, such as plasmids or bacteriophages, then replicated and harvested following introduction into suitable bacterial host cells. DNA or RNA fragments derived from isolated clones of the invention can also be used as probes for in situ hybridization in order to locate tissues which express this gene, or for other hybridization assays for the presence of the gene or an mRNA transcriped therefrom in various biological tissues. In addition, oligonucleotides complementary to the sequence of an isolated clone of the invention can be synthesized and used as probes for this gene, an mRNA associated therewith, or for the isolation of related genes by homology screening of genomic or cDNA libraries, or by the use of amplification techniques such as the Polymerase Chain Reaction.

This invention may also be used to obtain isoforms of the synapsin III protein, or fragments thereof, produced from expression of an isolated genomic clone. For example, an isolated clone of the invention, or fragments thereof can be subcloned into suitable expression vectors, such as the plasmid pET15b (Novagen, Madison, Wis.), and transfected into suitable host cells, such as bacteria, yeast, or mammalian cells. As a result, an isoform of the synapsin III protein can be produced in the transfected host cell, and recovered from the host for direct uses or for experimental study, using methods well known in the art. Furthermore, pursuant to the invention, either an entire isoform the synapsin III protein or fragments thereof can be recovered from the transfected host for further uses.

This invention may also be used to generate antibodies directed against isoforms of human synapsin III protein. Production of an isoform, e.g., synapsin IIIa, IIIb, or IIIc, or fragments thereof, encoded by an isolated clone in transfected host cells such as those described above, would provide an isoform of the synapsin III protein, or fragments thereof, which could be used as antigen for the generation of polyclonal or monoclonal antibodies against isoforms of a synapsin III protein, using methods well known in the art. These antibodies could be used to detect the presence of an isoform of synapsin III protein in humans or animals, or in biological tissues or fluids isolated from humans or animals.

In addition, this invention may be used to isolate transcriptional or translational regulatory elements from the 5' untranslated region of the synapsin III gene, or post-transcriptional regulatory elements from the 3' untranslated regions of the isolated gene.

This invention can further be used to detect mutations in the synapsin III gene in individuals who are at risk of developing schizophrenia. Identification of these mutations will allow one to determine which individuals are at risk for developing schizophrenia.

Accordingly, it is a principal object of the present invention to provide various isoforms of the synapsin III protein and subunits or fragments thereof in purified form that exhibit certain characteristics and activities associated with synapsin III promotion of neurotransmitter activity and synaptogenesis.

It is a further object of the invention to provide isolated nucleic acid molecules which encode various isoforms of synapsin III, e.g., synapsin IIIa, IIIb, and IIIc. These isolated nucleic acid molecules are produced from the alternative splicing of RNA complementary to the synapsin III gene.

It is a further object of the invention to provide isolated nucleic acid molecules hybridizable under standard hybridization conditions to an isolated nucleic acid molecule that encodes an isoform of a synapsin III protein.

It is a further object of the present invention to provide antibodies to isoforms of synapsin III and their subunits, and methods for their preparation, including recombinant means.

It is a further object of the present invention to provide a method for detecting the presence of an isoform of synapsin III and its subunits in mammals in which invasive, spontaneous, or idiopathic pathological states due to neurotransmission deficiencies are suspected to be present, especially schizophrenia.

It is a further object of the present invention to provide a method and associated assay system for screening substances such as drugs, agents and the like, potentially effective in either mimicking the activity or combating the adverse effects of an isoform of synapsin III and/or its subunits in mammals.

It is a still further object of the present invention to provide a method for the treatment of mammals to control the amount or activity of isoforms of the synapsin III protein, or subunits thereof, so as to alter the adverse consequences of such presence or activity, or where beneficial, to enhance such activity.

It is a still further object of the present invention to provide a method for the treatment of mammals to control the amount or activity of isoforms of synapsin III or subunits or fragments thereof, so as to treat or avert the adverse consequences of invasive, spontaneous or idiopathic pathological states, especially schizophrenia and other neurodegenerative diseases.

It is a still further object of the present invention to provide pharmaceutical compositions for use in therapeutic methods which comprise or are based upon isoforms of synapsin III, or subunits thereof, their binding partner(s), or upon agents or drugs that control the production, or that mimic or antagonize the activities of isoforms of synapsin III, i.e., synapsin IIIa, synapsin IIIb, or synapsin IIIc.

Other objects and advantages will become apparent to those skilled in the art from a review of the ensuing description which proceeds with reference to the following illustrative drawings.

BRIEF DESCRIPTION OF THE DRAWINGS

FIG. 4 is the cDNA sequence (upper) (SEQ ID NO: 2) and protein sequence (lower) (SEQ ID NO: 1) for synapsin IIIa.

FIG. 5 is a comparison of the protein sequences of synapsin IIIa to synapsins IIa and Ia.

FIG. 6b is a photograph of Northern blot analysis showing the distribution of synapsin III RNA in brain.

FIG. 7a is a photograph of a Western blot analysis showing expression of synapsin proteins in brain.

FIG. 8 is the amino acid sequence of synapsin IIIb (SEQ ID NO:6).

FIG. 9 is the nucleotide sequence of a nucleic acid molecule which encodes synapsin IIIb (SEQ ID NO:5).

FIG. 10 is the amino acid sequence synapsin IIIc (SEQ ID NO:8).

FIG. 11 is the nucleotide sequence of a nucleic acid molecule which encodes sequence of synapsin IIIc (SEQ ID NO:7).

DETAILED DESCRIPTION OF THE INVENTION

Figure 1:
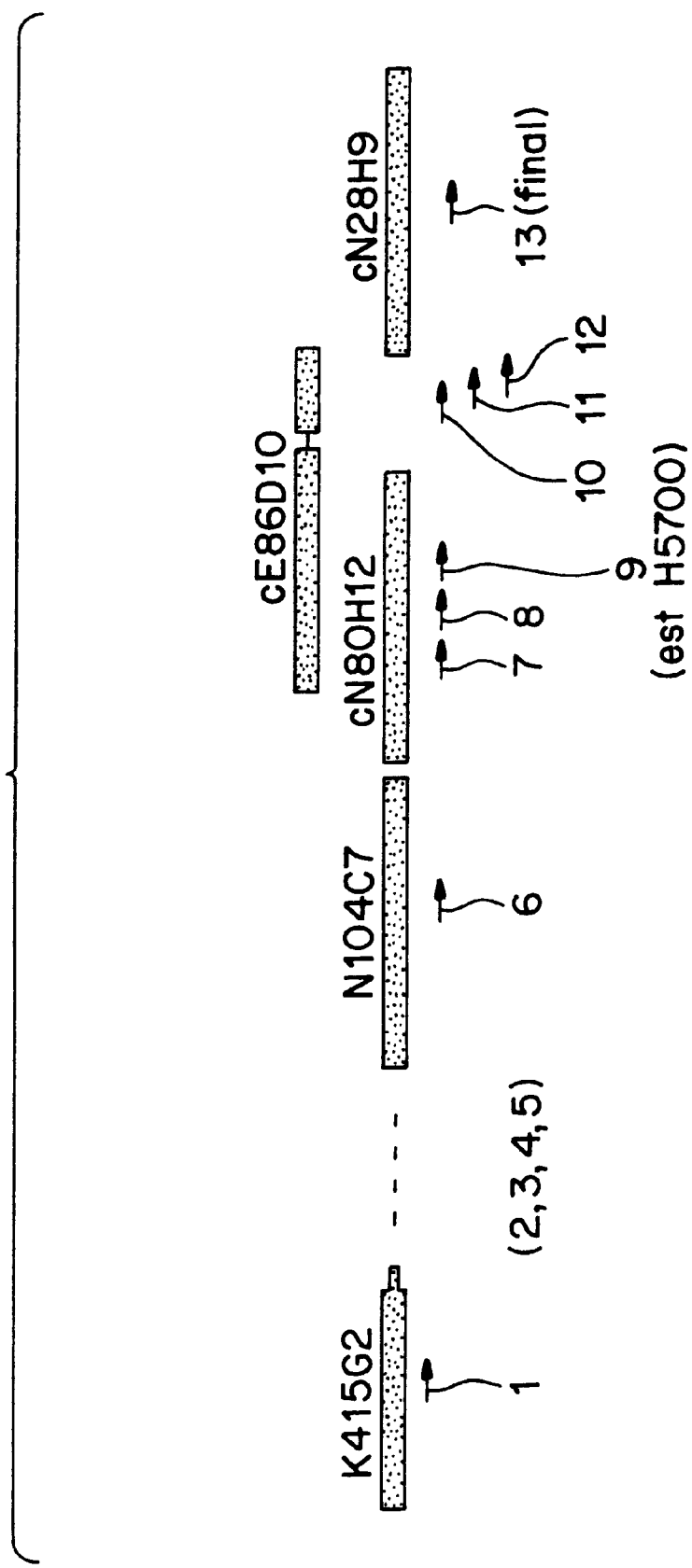
FIG. 1 depicts schematic diagram of chromosome 22, showing the location of exons of synapsin III on cosmids localized to this gene.

In its broadest aspect, the present invention extends to the isolation and characterization of an isoform of human synapsin III protein having the following characteristics:

a) it is localized to neurons and nerve terminals; and b) it is associated with synaptic vesicles.

In a specific example, an isoform of synapsin III of the invention comprises an amino acid sequence as shown in FIG. 4 (SEQ ID NO:1), FIG. 8 (SEQ ID NO:6), or FIG. 10 (SEQ ID NO:8).

In a particular embodiment, the present invention relates to all members of the herein disclosed family of synapsin III proteins.

The present invention also relates to a recombinant DNA molecule or cloned gene, or a degenerate variant thereof, which encodes an isoform of synapsin III protein; preferably a nucleic acid molecule, in particular a recombinant DNA molecule or cloned gene, encoding an isoform synapsin III protein and which has a nucleotide sequence or is complementary to a DNA sequence shown in FIG. 4 (SEQ ID NO:2), FIG. 9 (SEQ ID NO:5), or FIG. 11 (SEQ ID NO:8).

The human DNA sequences encoding isoforms of the synapsin III protein, or portions thereof, may be prepared as probes to screen for complementary sequences and genomic clones in the same or alternate species. The present invention extends to probes so prepared that may be provided for screening cDNA and genomic libraries for the presence of an isoform of synapsin III. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences set forth in FIG. 4 (SEQ ID NO:2), FIG. 9 (SEQ ID NO:5), or FIG. 11 (SEQ ID NO:7). Correspondingly, the preparation of antisense RNA and ribozymes are included herein.

The present invention also includes isoforms of synapsin III having the activities noted herein, and that display the amino acid sequences set forth and described above and selected from SEQ ID NO:1, SEQ ID NO:6 or SEQ ID NO:10.

In a further embodiment of the invention, an isolated nucleic acid molecule encoding an isoform of a synapsin III protein, may be operatively linked to an expression control sequence which may be introduced into an appropriate host. The invention accordingly extends to unicellular hosts transformed with a cloned gene or recombinant DNA molecule comprising a DNA sequence encoding an isoform of synapsin III, e.g., synpasin IIIa, synapsin IIIb, or synapsin IIIc, and more particularly, the complete DNA sequence determined from the sequences set forth above and in SEQ ID NO:2, SEQ ID NO:5, or SEQ ID NO:7.

According to other preferred features of certain preferred embodiments of the present invention, a recombinant expression system is provided to produce biologically active animal or human synapsin III isoforms.

The concept of an isoform of synapsin III contemplates that specific factors exist for correspondingly specific interacting protein such as an isoform of synapsin III and the like, as described earlier. Accordingly, the exact structure of each isoform of synapsin III will understandably vary so as to achieve this interacting protein and activity specificity. It is this specificity and the direct involvement of an isoform of synapsin III in the chain of events leading to schizophrenia, that offers the promise of a broad spectrum of diagnostic and therapeutic utilities.

The present invention naturally contemplates several means for preparation of an isoform of synapsin III, including as illustrated herein known recombinant techniques, and the invention is accordingly intended to cover such synthetic preparations within its scope. The isolation of cDNA and amino acid sequences disclosed herein facilitates the reproduction of an isoform of synapsin III by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate activity of isoforms of synapsin III of target mammalian cells by interrupting or potentiating an isoform of synapsin III. In one instance, the test drug could be administered to a cellular sample with the ligand that activates an isoform of synapsin III, or an extract containing an activated isoform of synapsin III, to determine its effect upon the binding activity of an isoform of synapsin III to any chemical sample (including DNA), or to the test drug, by comparison with a control.

The assay system could more importantly be adapted to identify drugs or other entities that are capable of binding to an isoform of synapsin III and/or synapsin III factors or proteins, either in the cytoplasm or in the nucleus, thereby inhibiting or potentiating synaptic activity, and modulating the schizophrenic symptoms in the mammal under treatment. Such assay would be useful in the development of drugs that would be specific against particular cellular activity, or that would potentiate such activity, in time or in level of activity. For example, such drugs might be used to modulate the schizophrenic symptoms, or to treat other pathologieent synapsin are believed to be a factor, as for example, schizophrenia.

In yet a further embodiment, the invention contemplates antagonists of the activity of an isoform of a synapsin III. In particular, an agent or molecule that inhibits an isoform of synapsin III. In a specific embodiment, the antagonist can be a peptide having the sequence of a portion of the M domain of a synapsin III.

The diagnostic utility of the present invention extends to the use an isoform of synapsin III in assays to screen for schizophrenia, and other pathologies wherein deficient neurotransmission is a causative factor.

The present invention likewise extends to the development of antibodies against isoforms of synapsin III, e.g., synapsin IIIa, synapsin IIIb, or synapsin IIIc, including naturally raised and recombinantly prepared antibodies. For example, the antibodies could be used to screen expression libraries to obtain the nucleic acid molecules that encode an isoform of synapsin III. Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating synapsis activity.

In particular, antibodies against specifically phosphorylated factors can be selected and are included within the scope of the present invention for their particular ability in following activated protein. Thus, activity of an isoform of synapsin III or of the specific polypeptides believed to be causally connected thereto may therefore be followed directly by the assay techniques discussed infra, through the use of an appropriately labeled quantity of a synapsin III of the invention, or antibodies or analogs thereof.

Thus, isoforms of synapsin III, their analogs and/or derivatives, and any antagonists or antibodies that may be raised thereto, are capable of use in connection with various diagnostic techniques, including immunoassays, such as a radioimmunoassay, using for example, an antibody to an isoform of synapsin III of the invention that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

For example, antibodies against specifically phosphorylated factors may be selected and appropriately employed in the exemplary assay protocol, for the purpose of following activated protein as described above.

In the instance where a radioactive label, such as the isotopes $^{3}H$, $^{14}C$, $^{32}p$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be u accomplished by any of the presently utilized colorimetric, spectrophotometric, fluorospectrophotometric, amperometric or gasometric techniques known in the art, The present invention includes an assay system which may be prepared in the form of a test kit for the quantitative analysis of the extent of the presence of an isoform of synapsin III, or to identify drugs or other agents that may mimic or block the activity of an isoform of synapsin III. The system or test kit may comprise a labeled component prepared by one of the radioactive and/or enzymatic techniques discussed herein, coupling a label to an isoform of synapsin III, agonists and/or antagonists thereof, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of an isoform of synapsin III, its subunits, or active fragments thereof, or upon agents or other drugs determined to possess the same activity. A first therapeutic method is associated with the prevention of the manifestations of conditions causally related to or following from the binding activity of an isoform of synapsin III or its subunits, and comprises administering an agent capable of modulating the production and/or activity of an isoform of synapsin III or subunits thereof, either individually or in mixture with each other in an amount effective to prevent the development of those conditions in the host. For example, drugs or other binding partners to an isoform of synapsin III protein may be administered to inhibit or potentiate neurotransmitter activity, as in the treatment of schizophrenia.

Also, the blockade of the action of specific tyrosine phosphatases in the dephosphorylation of activated (phosphorylated) synapsin III proteins, e.g., isoforms of synapsin III, present a method for potentiating the activity of an isoform of synapsin III protein that would concomitantly potentiate therapies based on synapsin III protein activation.

More specifically, the therapeutic method generally referred to herein could include the method for the treatment of various pathologies or other cellular dysfunctions and derangements by the administration of pharmaceutical compositions that may comprise effective inhibitors or enhancers of activation of an isoform of synapsin III such as synapsin IIIa, IIIb, or IIIc, or their subunits, or other equally effective drugs developed for instance by a drug screening assay prepared and used in accordance with a further aspect of the present invention. For example, drugs or other binding partners to an isoform of synapsin III, as represented by SEQ ID NO:1, SEQ ID NO:6 or SEQ ID NO:8, may be administered to inhibit or potentiate neurotransmitter activity.

In particular, the proteins of synapsin III whose sequences are presented in SEQ ID NO:1, SEQ ID NO:6, or SEQ ID NO:8 set forth herein, their antibodies, agonists, antagonists, or active fragments thereof, could be prepared in pharmaceutical formulations for administration in instances wherein modulation of neurotransmission is appropriate, such as to treat various pathologies where such modulation is desirable.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The term "synapsin III generally refers, refer to proteinaceous materials which are isoforms of synapsin III, and extend to those proteins having the amino acid sequence data described herein and presented in FIG. 4 (SEQ ID NO:1), FIG. 8 (SEQ ID NO:6), and FIG. 10 (SEQ ID NO:8), and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "synapsin IIIa", "synapsin IIIb", and "synapsin IIIc" are intended to include within their scope proteins specifically recited herein as well as all substantially homologous analogs and allelic variations.

Furthermore, as used herein, the term "isoform" refers to multiple forms of the same protein that differ somewhat in their amino acid sequence. They can be produced by different genes or by alternative splicing of RNA transcripts from the same gene. As set forth herein, synapsin IIIa, IIIb, and IIIc (SEQ ID Nos: 1, 5 and 6 respectively) are isoforms of the synapsin III protein, and are produced from transcription of the synapsin III gene.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are isolated nucleic acid molecules which encode isoforms of synapsin III having an amino acid sequence of SEQ ID NO:1, SEQ ID NO:6, and SEQ ID NO:8, but which are degenerate to SEQ ID NO:2, SEQ ID NO:5, and SEQ ID NO:7. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |

-continued

| | |
|---|---|
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in SEQ ID NO:2, SEQ ID NO:5 and SEQ ID NO:7 such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups

Alanine

Valine

Leucine

Isoleucine

Proline

Phenylalanine

Tryptophan

Methionine

Amino Acids with Uncharged Polar R Groups

Glycine

Serine

Threonine

Cysteine

Tyrosine

Asparagine

Glutamine

Amino Acids with Charged Polar R Groups (negatively charged at Ph 6.0)

Aspartic acid

Glutamic acid

Basic Amino Acids (positively charged at pH 6.0)
Lysine
Arginine
Histidine (at pH 6.0)

Another grouping may be those amino acids with phenyl groups:
Phenylalanine
Tryptophan
Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous when at least about 70% of the amino acid residues (preferably at least about 80%, and most preferably at least about 90 or 95%) are identical, or represent conservative substitutions.

A "heterologous" region of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in symptoms related to schizophrenia, such as hallucinations, delusions, bizarre behavior, though disorder, lack of motivation, social withdrawal and apathy.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control ion of the desired product encoded by the DNA sequence. If a gene that one desires to insert into a recombinant DNA molecule does not contain an appropriate start signal, such a start signal can be inserted in front of the gene.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 15 nucleotides; and more preferably the length is at least about 20 nucleotides; and most preferably 30 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 15 nucleotides; and more preferably the length is at least about 30 nucleotides; and most preferably 40 nucleotides.

In a specific embodiment, the term "standard hybridization conditions" refers to a $T_m$ of 55 ° C., and utilizes conditions as set forth above. In a preferred embodiment, the $T_m$ is 60° C.; in a more preferred embodiment, the $T_m$ is 65° C.

In its primary aspect, the present invention concerns the identification of an isoform of synapsin III, e.g., synpasin IIIa, synapsin IIIb, and synapsin IIIc.

As stated above, the present invention also relates to a recombinant DNA molecule or cloned gene, or a degenerate variant thereof, which encodes an isoform of synapsin III, or a fragment thereof, comprising an amino acid sequence set forth in FIG. 4 (SEQ ID NO:1), FIG. 8 (SEQ ID NO:5) or FIG. 10 (SEQ ID NO:8); preferably an isolated nucleic acid molecule, in particular a recombinant DNA molecule or cloned gene, encoding an isoform of synapsin III having, wherein the nucleic acid molecule comprises a DNA sequence a nucleotide sequence or is complementary to a DNA sequence of the invention shown in FIG. 4 (SEQ ID NO:2), FIG. 9 (SEQ ID NO:5), or FIG. 11 (SEQ ID NO:7).

The possibilities both diagnostic and therapeutic that are raised by the existence of an isoform of synapsin III, derive from the fact that factors of isoforms of synapsin III appear to participate in direct and causal protein-protein interaction between isoforms of synapsin III, and those factors that thereafter affect neurotransmission. As suggested earlier and elaborated further on herein, the present invention contemplates pharmaceutical intervention in the cascade of reactions in which an isoform of synapsin III is implicated, to modulate the activity initiated by an isoform of synapsin III.

Thus, in instances where it is desired to reduce or inhibit the resulting from a particular stimulus or factor, an appropriate inhibitor of an isoform of synapsin III, e.g., an inhibitor of synapsin IIIa, synapsin IIIb, or synapsin IIIc, could be introduced to block the interaction of an isoform of synapsin III with those factors causally connected with synapsin III. Correspondingly, instances where insufficient neurotransmission is taking place could be remedied by the introduction of additional quantities of an isoform of synapsin III or its chemical or pharmaceutical cognates, analogs, fragments and the like.

As discussed earlier, isoforms of synapsin III, their binding partners or other ligands or agents exhibiting either mimicry or antagonism thereto or control over their production, may be prepared in pharmaceutical compositions, with a suitable carrier and at a strength effective for administration by various means to a patient experiencing an adverse medical condition associated with an isoform of synapsin III for the treatment thereof. A variety of administrative techniques may be utilized, among them parenteral techniques such as subcutaneous, intravenous and intraperitoneal injections, catheterizations and the like. Average quantities of an isoform of synapsin III or its subunits may vary and in particular should be based upon the recommendations and prescription of a qualified physician or veterinarian.

Also, antibodies including both polyclonal and monoclonal antibodies, and drugs that modulate the production or activity of an isoform of a synapsin III and/or its subunits may possess certain diagnostic applications and may for example, be utilized for the purpose of detecting and/or measuring conditions such as viral infection or the like. For example, an isoform of synapsin III or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of an isoform of synapsin III of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against peptides of isoforms of synapsin III can be screened for various properties; i.e., isotope, epitope, affinity, etc. Of particular interest are monoclonal antibodies that neutralize the activity of an isoform of synapsin III or its subunits. Such monoclonals can be readily identified in synapsin III activity assays. High affinity antibodies are also useful when immunoaffinity purification of a native or recombinant isoform of synapsin III is possible.

Preferably, an anti-synapsin III antibody, i.e., an antibody made against an isoform of synapsin III, used in the diagnostic methods of this invention is an affinity purified polyclonal antibody. More preferably, the antibody is a monoclonal antibody (mAb). In addition, it is preferable for an anti-synapsin III antibody molecule, e.g., an antibody made against an isoform of synapsin III, used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to an isoform of a synapsin III/protein, such as an anti-synapsin III antibody, preferably an affinity-purified polyclonal antibody, and more preferably a mAb. As previously discussed, patients capable of benefiting from this method include those suffering from hallucinations, delusions, bizare behavior and thought disorder, as well as negative symptoms such as lack of motivation, social withdrawal and apathy. Methods for isolating the synapsin III and inducing anti-synapsin III antibodies and for determining and optimizing the ability of anti-synapsin III antibodies to assist in the examination of the target cells are all well-known in the art.

Methods for producing polyclonal anti-polypeptide antibodies are well-known in the art. See U.S. Pat. No. 4,493, 795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference in its entirety. Briefly, to form the hybridoma from which the monoclonal antibody composition is produced, a myeloma or other self-perpetuating cell line is fused with lymphocytes obtained from the spleen of a mammal hyperimmunized with the binding portion of an isoform of synapsin III or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with an isoform of synapsin III and their ability to inhibit specified synapsin III activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal antibodies against isoforms of synapsin III are also well-known in the art. See Niman et al., *Proc. Natl. Acad. Sci. USA*, 80:4949–4953 (1983). Typically, an isoform of synapsin III or a peptide analog is used either alone or conjugated to an immunogenic carrier, as the immunogen in the before described procedure for producing anti-synapsin III monoclonal antibodies. The hybridomas are screened for the ability to produce an antibody that immunoreacts with an isoform of a synapsin III, or a peptide analog or fragment of an isoform of a synapsin III.

The present invention further contemplates therapeutic compositions useful in practicing the therapeutic methods of this invention. A subject therapeutic composition includes, in admixture, a pharmaceutically acceptable excipient (carrier) and one or more isoforms of a synapsin III, polypeptide analog thereof or fragment thereof, as described herein as an active ingredient. In a preferred embodiment, the composition comprises an antigen capable of modulating the specific binding of an isoform of synapsin III within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of synapsin III binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Exemplary formulations are given below:

| Formulations | |
|---|---|
| Ingredient | mg/ml |
| Intravenous Formulation I | |
| isoform of synapsin III | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| analog of synapsin III | 10.0 |
| sodium bisulfite USP | 3.2 |
| disodium edetate USP | 0.1 |
| water for injection q.s.a.d. | 1.0 ml |
| Intravenous Formulation III | |
| analog of synapsin III | 10.0 |
| sodium bisulfite USP | 3.2 |
| disodium edetate USP | 0.1 |
| water for injection q.s.a.d. | 1.0 ml |
| Intravenous Formulation IV | |
| analog of synapsin III | 10.0 |
| dextrose USP | 45.0 |

| -continued | |
|---|---|
| Formulations | |
| Ingredient | mg/ml |
| sodium bisulfite USP | 3.2 |
| edetate disodium USP | 0.1 |
| water for injection q.s.a.d. | 1.0 ml |
| Intravenous Formulation V | |
| antagonist of an isoform of synapsin III | 5.0 |
| sodium bisulfite USP | 3.2 |
| disodium edetate USP | 0.1 |
| water for injection q.s.a.d. | 1.0 ml |

As used herein, "pg" means picogram, "ng" means nanogram, "ug" or "µg" mean microgram, "mg" means milligram, "ul" or "µl" mean microliter, "ml" means milliliter, "l" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., $E.\ coli$ plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. Especially useful is the expression vector which is the plasmid pET15b (Novagen, Madison, Wis.).

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC systator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of $E.\ coli$, Pseudomonas, Bacillus, Streptomyces, fungi such as yeasts, and animal cells, such as CHO, R1.1B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that analogs of isoforms of synapsin III may be prepared from nucleotide sequences of the protein complex/subunit derived within the scope of the present invention. Analogs, such as fragments, may be produced, for example, by pepsin digestion of synapsin III material. Other analogs, such as muteins, can be produced by standard site-directed mutagenesis of nucleic acids encoding isoforms of synapsin III, such as an isolated nucleic acid of FIG. 4 (SEQ ID NO:2), FIG. 9 (SEQ ID NO:5), or FIG. 11 (SEQ ID NO:7). Analogs exhibiting "synapsin III activity" such as small molecules, whether functioning as promoters or inhibitors, may be identified by known in vivo and/or in vitro assays.

As mentioned above, an isolated nucleic acid molecule encoding an isoform of synapsin III can be prepared synthetically rather than cloned. The molecule can be designed with the appropriate codons for an isoform of the synapsin III. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic nucleic acid molecules allow convenient construction of genes which will express analogs or "muteins" of isoforms of synapsin III. Alternatively, DNA encoding muteins can be made by site-directed mutagenesis of native synapsin III genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids.

The present invention further extends to the preparation of antisense oligonucleotides and ribozymes that may be used to interfere with the expression of an isolated nucleic acid molecule encoding an isoform of synapsin III at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into cells producing isoforms of synapsin III. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs encoding isoforms of synapsin III, and their ligands.

The present invention also relates to a variety of diagnostic applications, including methods for detecting the presence of stimuli such as the earlier referenced interacting proteins by reference to their ability to elicit the activities which are mediated by an isoform of synapsin III. As mentioned earlier, isoforms of synapsin III can be used to produce antibodies to themselves by a variety of known techniques, and such antibodies could then be isolated and utilized as in tests for the presence of particular synapsin III activity in suspect target cells.

As described in detail above, antibody(ies) to an isoform of synapsin III can be produced and isolated by standard methods including the well known hybridoma techniques. For convenience, the antibody(ies) to an isoform of synapsin III will be referred to herein as $Ab_1$ and antibody(ies) raised in another species as $Ab_2$.

The presence of an isoform of synapsin III in cells can be ascertained by the usual immunological procedures applicable to such determinations. A number of useful procedures are known. Three such procedures which are especially useful utilize either an isoform of synapsin III labeled with a detectable label, antibody $Ab_1$ labeled with a detectable label, or antibody $Ab_2$ labeled with a detectable label. The procedures may be summarized by the following equations wherein the asterisk indicates that the particle is labeled, and "synIII" stands for an isoform of synapsin III:

A. $synIII^* + Ab_1 = synIII^*Ab_1$
B. $synIII + Ab^* \ synIIIAb_1^*$
C. $synIII + Ab_1 + Ab_2^* = synIIIAb_1Ab_2^*$ The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, an isoform of synapsin III forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-synapsin III antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

An isoform of synapsin III or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the be ascertained.

Accordingly, a purified quantity of an isoform of synapsin III, e.g., synapsin IIIa, synapsin IIIb or synapsin IIIc may be radiolabeled and combined, for example, with antibodies or other inhibitors thereto, after which binding studies would be carried out. Solutions would then be prepared that contain various quantities of labeled and unlabeled uncombined synapsin III, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

Another assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves acompared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical professional may be prepared to determine the presence or absence of predetermined synapsin III activity or predetermined synapsin III activity capability in suspected target cells. In accordance with the testing techniques discussed above, one class of such kits will contain at least a labeled isoform of synapsin III or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined synapsin III activity, comprising:

(a) a predetermined amount of at least one labeled immunochemically reactive component obtained by the direct or indirect attachment of a factor of an isoform of synapsin III or a specific binding partner thereto, to a detectable label;
(b) other reagents; and
(c) directions for use of said kit.

More specifically, the diagnostic test kit may comprise:
(a) a known amount of an isoform of synapsin III as described above (or a binding partner) generally bound to a solid phase to form an immunosorbent, or in the alternative, bound to a suitable tag, or plural such end products, etc. (or their binding partners) one of each;
(b) if necessary, other reagents; and
(c) directions for use of said test kit.

In a further variation, the test kit may be prepared and used for the purposes stated above, which operates according to a predetermined protocol (e.g. "competitive," "sandwich," "double antibody," etc.), and comprises:
(a) a labeled component which has been obtained by coupling an isoform of synapsin III to a detectable label;
(b) one or more additional immunochemical reagents of which at least one reagent is a ligand or an immobilized ligand, which ligand is selected from the group consisting of:
  (I) a ligand capable of binding with the labeled component (a);
  (ii) a ligand capable of binding with a binding partner of the labeled component (a);
  (iii) a ligand capable of binding with at least one of the component(s) to be determined; and
  (iv) a ligand capable of binding with at least one of the binding partners of at least one of the component(s) to be determined; and
(c) directions for the performance of a protocol for the detection and/or determination of one or more components of an immunochemical reaction between the synapsin III and a specific binding partner thereto.

The present invention also includes a test kit for genetic screening which can be utilized to identify mutations an isoform of synapsin III or its encoding cDNA. By identifying patients with mutated synapsin III DNA and comparing the mutation to a base developed by correlating a particular mutation in an isoform of synapsin III with a particular neuropsychiatric state or disease, identification and/or confirmation of, a particular neuropsychiatric state or disease can be made. Accordingly, such a kit would comprise a PCR-based test that would involve transcribing the patients mRNA with a specific primer, and amplifying the resulting cDNA using another set of primers. The amplified product would be detectable by gel electrophoresis and could be compared with known standards for the various isoforms of synapsin III. Accordingly, such a kit would utilize a patient's blood or serum sample and the DNA would be extracted using standard techniques. Primers flanking a known mutation are then used to amplify a piece of the synapsin III gene.

The amplified piece would then be sequenced to determine the presence of a mutation.

In accordance with the above, an assay system for screening potential drugs effective to modulate the activity of an isoform of synapsin III may be prepared. A particular isoform synapsin III may be introduced into a test system, and the prospective drug may also be introduced into the resulting cell culture, and the culture thereafter examined to observe any changes in activity of an isoform of synapsin III in the cells, due either to the addition of the prospective drug alone, or due to the effect of added quantities of an isoform of synapsin III.

PRELIMINARY CONSIDERATIONS

The following examples are presented in order to more fully illustrate the preferred embodiments of the invention. They should in no way be construed, however, as limiting the broad scope of the invention.

EXAMPLE 1

Experimental Details
Searching for Exons in Chromosome 22

Figure 2:
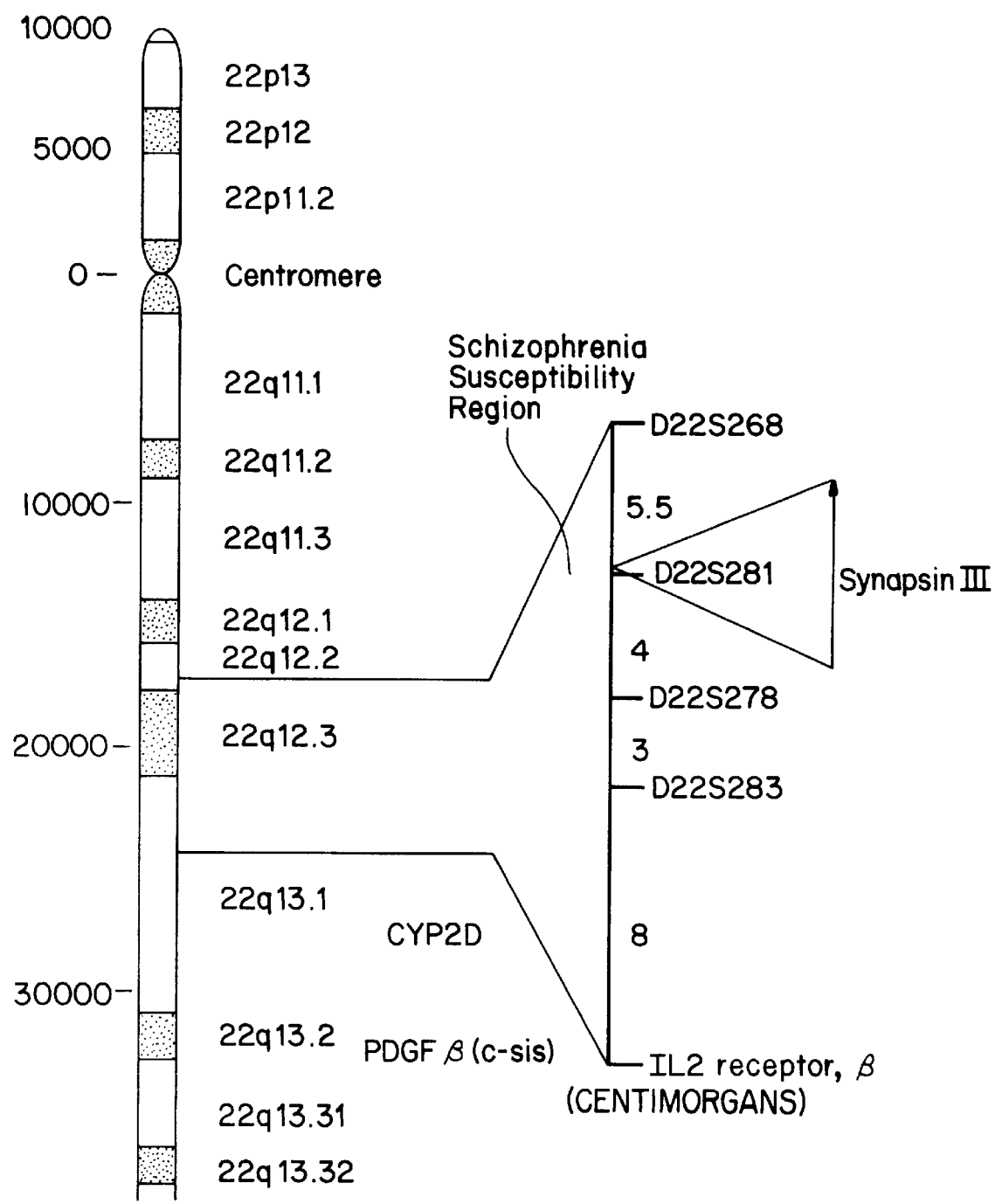
FIG. 2 is a schematic diagram of chromosome 22, showing the location of the synapsin III gene within the schizophrenia susceptibility region.

Homology to a highly conserved exon of synapsin I and II, exon 9, was observed in a small region of chromosome 22, known as H5770. This region of chromosome 22 has been studied intensively because of its possible association with human disease, and is currently being sequenced as part of the human genome project. Cosmid sequences flanking the initial observed region of homology were identified and searched for other homologous exons. Eventually, 9 out of 13 exons of a new synapsin were discovered in this region of chromosome 22 (FIG. 1). This region of chromosome 22 was previously identified as one that would likely contain a susceptibility gene for schizophrenia (9–17) (FIG. 2 and Table 1, below).

TABLE 1

Reported Significance of Linkage Among Various Studies

| D22S Marker | Coon et al, 1994 | Polymeropoulos et al, 1994 | Vallada et al, 1995a | Vallada et al, 1995b | Kalsi et al., 1995 | Moises et al. 1995* | Lasseter et al., 1995 | Schwab et al, 1995 | Gill et al, 1996 |
|---|---|---|---|---|---|---|---|---|---|
| 264 | | | 0.14 | | | | 0.015 | | |
| 315 | 0.299 | ns | | | | | | | |
| 268 | | | 0.46 | 0.017 | | | 0.105 | | |
| 304 | | | | | | | | 0.068 | |
| 281 | 0.656 | 0.026 | | | | | | | |
| 278 | 0.312 | 0.019 | 0.01 | 0.008 | | 0.02 | 0.003 | | 0.001 |
| 283 | 0.730 | 0.017 | 0.001 | 0.005 | 0.696 | | 0.013 | | |
| IL2R β | 0.557 | ns | 0.43 | | | | 0.046 | 0.382 | |
| 279 | 0.20 | 0.042 | | | | | | | |
| 276 | 0.016 | ns | | | | | | | |
| CYP2D | 0.221 | | 0.11 | | | | | | |
| 270 | 0.118 | ns | | | | | | | |
| 307 | | | 0.71 | | | | 0.162 | | |

TABLE 1-continued

Reported Significance of Linkage Among Various Studies

| D22S Marker | Coon et al, 1994 | Polymeropoulos et al, 1994 | Vallada et al, 1995a | Vallada et al, 1995b | Kalsi et al., 1995 | Moises et al. 1995* | Lasseter et al., 1995 | Schwab et al, 1995 | Gill et al, 1996 |
|---|---|---|---|---|---|---|---|---|---|
| 282 | | | | 0.05 | | | | | |
| 274 | 0.043 | ns | | 0.64 | 0.831 | | | | | ns = not significant
If blank, D22S marker was not analyzed.
*TDT analysis (transmission disequilibrium test). All other figures are reported significance of sib pair analyses.

The existence of homologous synapsin sequences in genomic DNA, however, does not necessarily mean that it is functional. Nonfunctional genes do exist in the human genome and are termed pseudogenes. To demonstrate that the new synapsin sequence was transcribed and expressed, it was demonstrated that spliced, mature RNA existed. It was further assumed, as with like other synapsins, that this new synapsin was expressed in brain.

Figure 3:
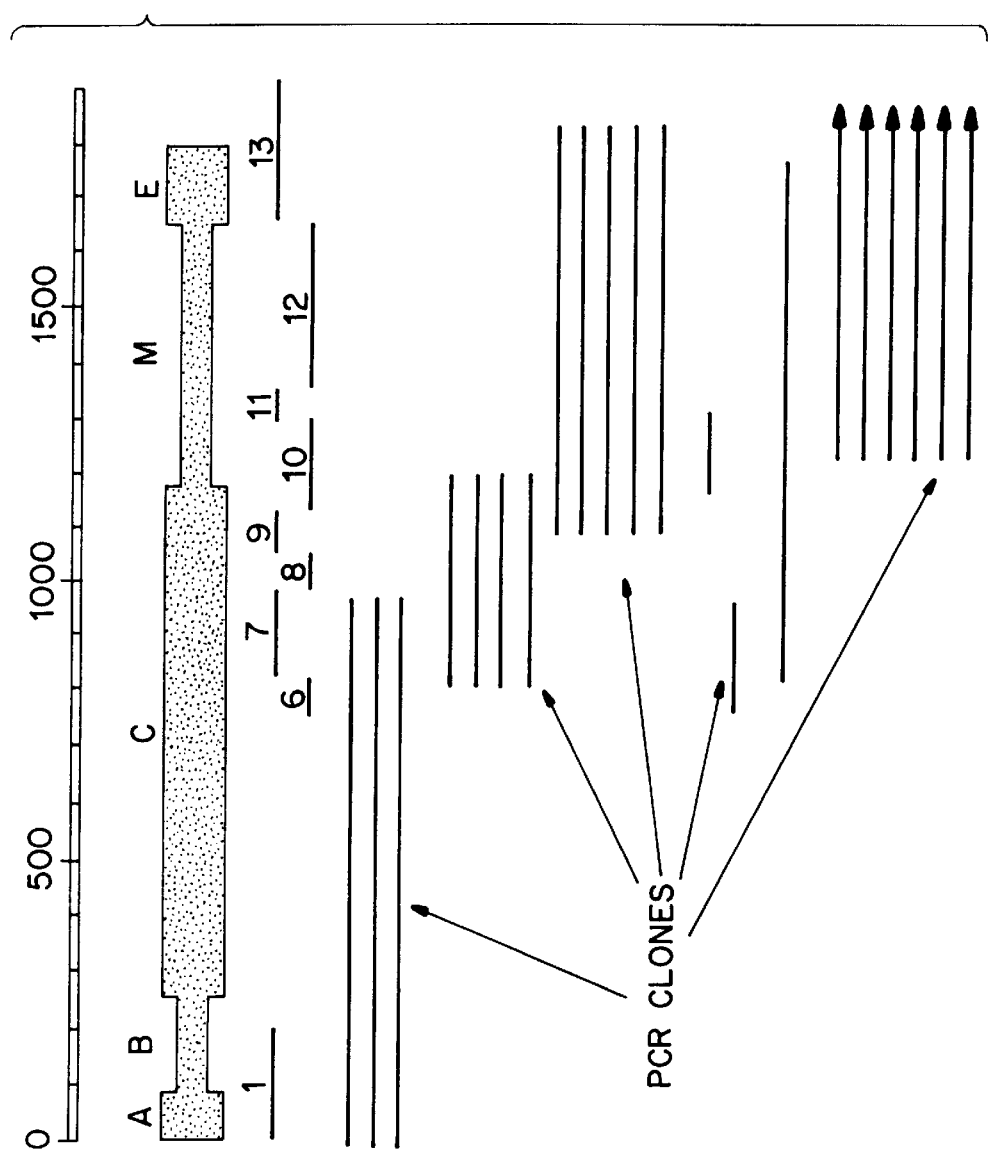
FIG. 3 is a diagram illustrating the clones spanning the entire length of the Synapsin III gene.

Poly A+ human brain RNA was obtained from Clonetech, and the RNA was reverse transcribed using random primers (23). The resulting cDNA served as a template for PCR using various primer pairs spanning different sets of exons. As depicted in FIG. 3, three PCR products were generated spanning the entire coding region of synapsin III. The sequence deduced from these PCR products is consistent with the existence of transcribed, spliced mature mRNA corresponding to synapsin III in human brain.

This confirms that the synapsin III gene is not a pseudogene, but a functional gene which gives rise to a protein in the brain.

Sequence of Synapsin III

Sequencing of the synapsin III gene revealed a novel DNA molecule encoding isoforms of the human synapsin III protein, e.g., synapsin IIIa, IIIb and IIIc. Synapsin IIIa is homologous to the known DNA sequences which encode the human synapsin I and synapsin II protein. One region of synapsin III, known as domain M, bears no homology to the other synapsins, and no homology to other proteins in Genbank.

The nucleotide sequence (upper sequence) and deduced amino acid sequence (lower sequence) of human synapsin IIIa is depicted in FIG. 4. The protein sequence of synapsin IIIa is compared to synapsins IIa and Ia in FIG. 5.

EXAMPLE 2

Figure 6A:
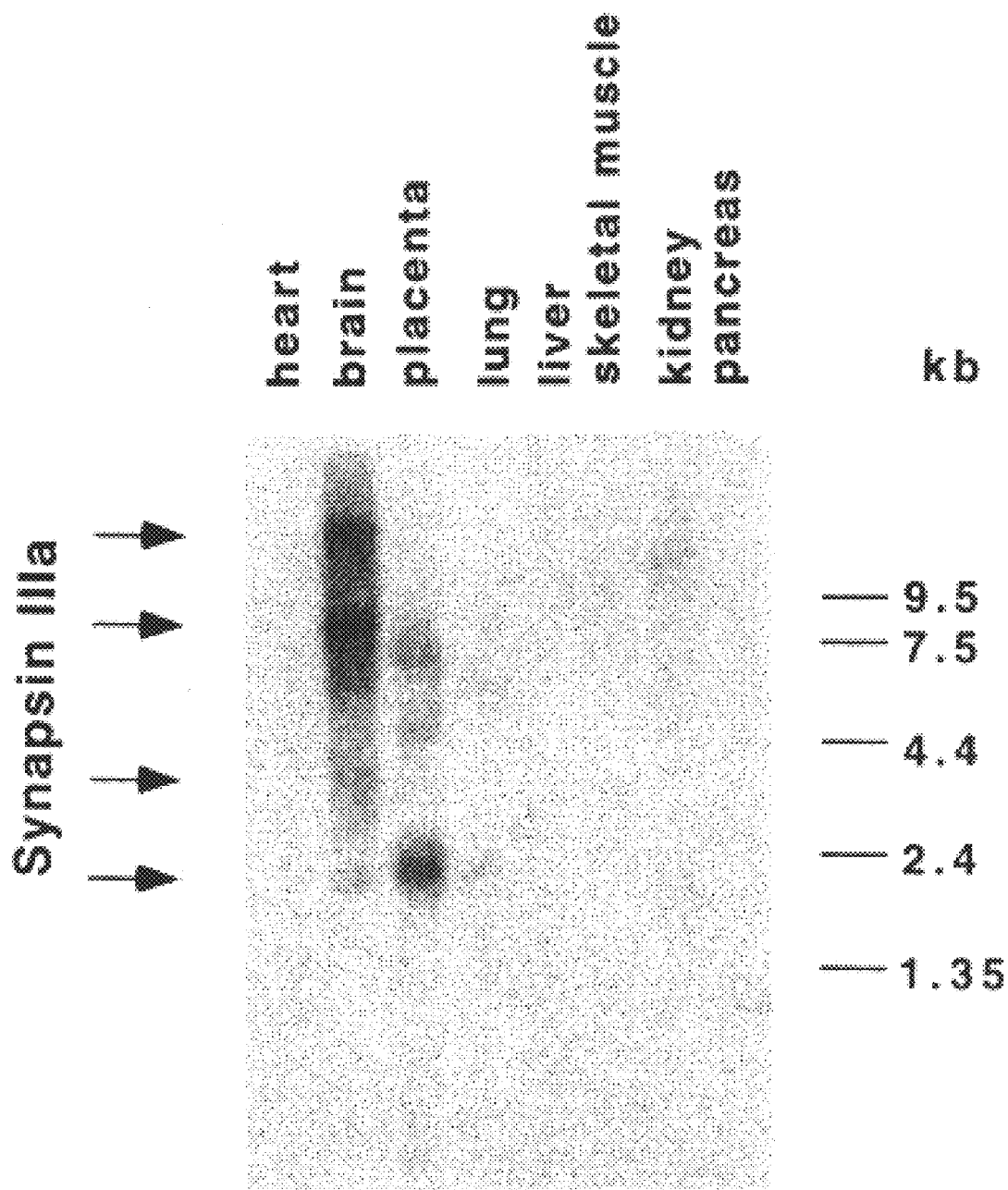
FIG. 6a is a photograph of Northern blot analysis showing the distribution of synapsin III RNA different tissues.
Figure 7B:
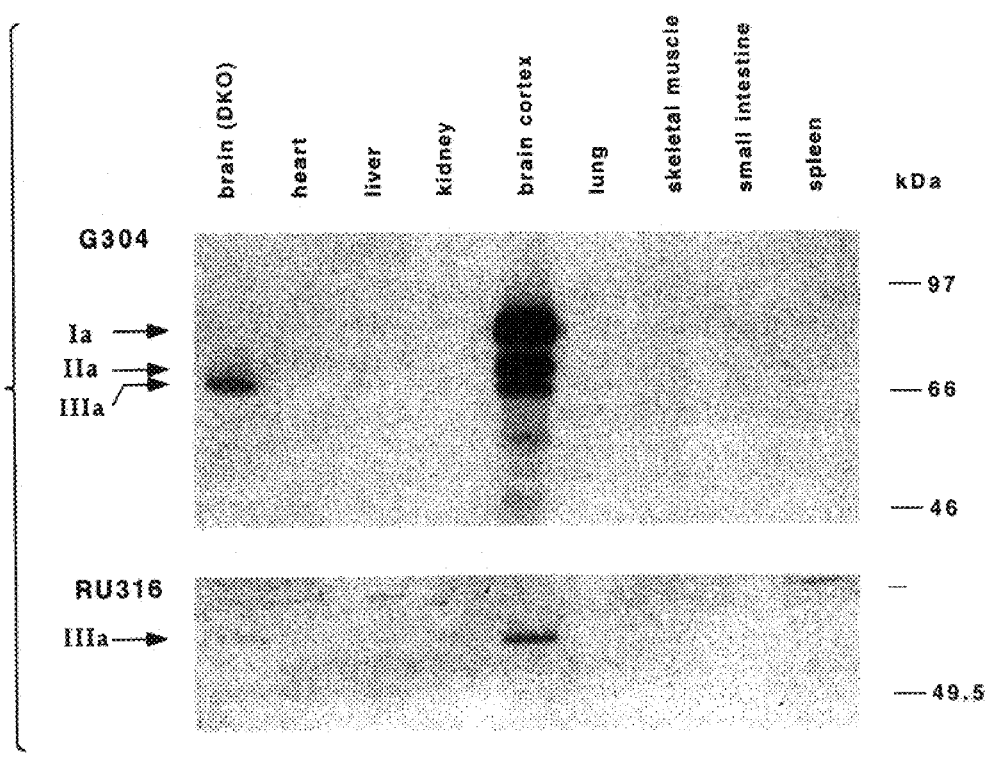
FIG. 7b is a photograph of a Western blot analysis showing the expression of synapsin protein in different tissues.

Northern blot analysis demonstrating tissue specific distribution and brain localization. Photographs of Northern blots demonstrating tissue specific distribution and brain localization of synapsin IIIa RNA are set forth in FIG. 6a and FIG. 6b respectively. Moreover, Western blots were prepared to determine expression of synapsin IIIa in brain and in different tissues. Photographs of those blots are set forth in FIG. 7a and FIG. 7b respectively.

EXAMPLE 3

Premade human northern blots from Clonetech were hybridized to a probe derived from the 3' UTR of human synapsin III. Hybridization and wash conditions were performed according to the manufacturer's specification.

EXAMPLE 4

Example 3 demonstrates that the antibody G304, which recognizes domain E of all synapsins, can recognize synapsins Ia, IIa, and IIIa migrate together.

Various mouse brain regions were dissected, homogenized, and boiled in 1% SDS. 100 μg of protein were electrophoresed on 7.5% SDS polyacrylamide gels, and electroblotted onto a nitrocellulose filter. The resulting western blot was then incubated with anti-synapsin antibody (G304; 1:5000 dilution) which detects all three synapsins, followed by incubation with alkaline phosphatase-conjugated goat anti-rabbit antibody. The blot was developed using the alkaline phosphatase substrates NBT and BCIP.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The documents should be considered as incorporated by reference in their entirety.

1. Sudhof, T. C., Czernik, A. J., Kao, H. T., Takei, K., Johnston, P. A., Horiuchi, A., Kanazir, S. D., Wagner, M. A., Perin, M. S., De Camilli, P. & Greengard, P. (1989). Synapsins: mosaics of shared and individual domains in a family of synaptic vesicle phosphoproteins. Science 245, 1474–80.
2. Greengard, P., Valtorta, F., Czernik, A. J. & Benfenati, F. (1993). Synaptic vesicle phosphoproteins and regulation of synaptic function. Science 259, 780–5.
3. Ferreira, A., Kosik, K. S., Greengard, P. & Han, H. Q. (1994). Aberrant neurites and synaptic vesicle protein deficiency in synapsin II-depleted neurons. Science 264, 977–9.
4. Ferreira, A., Han, H. Q., Greengard, P. & Kosik, K. S. (1995). Suppression of synapsin II inhibits the formation and maintenance of synapses in hippocampal culture. Proc. Natl. Acad. Sci. USA 92, 9225–9.
5. Ferreira, A., Li, L., Chin, L. -S., Kosik, K. S. & Greengard, P. (1997). Distinct roles of synapsin I and synapsin II during neuronal development.
6. Han, H. Q., Nichols, R. A., Rubin, M. R., Bahler, M. & Greengard, P. (1991). Induction of formation of presynaptic terminals in neuroblastoma cells by synapsin IIb. Nature 349, 697–700.
7. Lu, B., Greengard, P. & Poo, M. M. (1992). Exogenous synapsin I promotes functional maturation of developing neuromuscular synapses. Neuron 8, 521–9.
8. Schaeffer, E., Alder, J., Greengard, P. & Poo, M. M. (1994). Synapsin IIa accelerates functional development of neuromuscular synapses. Proc. Natl. Acad. Sci. USA 91, 3882–6.
9. Coon, H., Holik, J., Hoff, M., Reimherr, F., Wender, P., Myles-Worsley, M., Waldo, M., Freedman, R. & Byerley, W. (1994). Analysis of chromosome 22 markers in nine schizophrenia pedigrees. Am. J. Med. Genetics 54, 72–9.
10. Gill, M., Vallada, H., Collier, D., Sham, P., Holmans, P., Murray, R., McGuffin, P., Nanko, S., Owen, M., Antonarakis, S., Housman, D., Kazazian, H., Nestadt, G., Pulver, A. E., Straub, R. E., MacLean, C. J., Walsh, D., Kendler, K. S., DeLisi, L., Polymeropoulos, M., Coon, H., Byerley, W., Lofthouse, R., Gershon, E., Golden, L., Crow, T., Byerley, W., Coon, H., Freedman, R., Laurent, C., Bodeau-Pean, S., d'Amato, T., Jay, M., Campion, D., Mallet, J., Wildenauer, D. B., Lere, B., Albus, M., Ackenheil, M., Ebstein, R. P., Hallmayer, J., Maier, W., Gurling, H., Curtis, D., Gusharon, K., Brynjolfsson, J., Sigmundson, T., Petursson, H., Blackwood, D., Muir, W., St. Clair, D., He, L., Maguire, S., Moises, H. W., Hwu, H. -G., Yang, L., Wiese, C., Tao, L., Liu, X., Kristbjarnason, H., Levinson, D. F., Mowry, B. J., Donis-Keller, H., Hayward, N. K., Crowe, R. R., Silverman, J. M., Nancarrow, D. J., Read, C. M. (1996). A combined analysis of D22S278 marker alleles in affected sib-pairs: support for a susceptibility locus for schizophrenia at chromosome 22q12. Schizophrenia Collaborative Linkage Group (Chromosome 22). Am. J. Med. Genetics 67, 40–5.
11. Lasseter, V. K., Pulver, A. E., Wolyniec, P. S., Nestadt, G., Meyers, D., Karayiorgou, M., Housman, D., Antonarakis, S., Kazazian, H., Kasch, L., Babb, R., Kimberland, M. & Childs, B. (1995). Follow-up report of potential linkage for schizophrenia on chromosome 22q: Part 3. Am. J. Med. Genetics 60, 172–3.
12. Moises, H. W., Yang, L., Li, T., Havsteen, B., Fimmers, R., Baur, M. P., Liu, X. & Gottesman, I. I. (1995). Potential linkage disequilibrium between schizophrenia and locus D22S278 on the long arm of chromosome 22. Am. J. Med. Genetics 60, 465–7.
13. Polymeropoulos, M. H., Coon, H., Byerley, W., Gershon, E. S., Goldin, L., Crow, T. J., Rubenstein, J., Hoff, M., Holik, J., Smith, A. M., Shields, G., Bass, N. J., Poulter, M., Lofthouse, R., Vita, A., Morganti, C., Merril, C. R. & DeLisi, L. E. (1994). Search for a schizophrenia susceptibility locus on human chromosome 22. Am. J. Med. Genetics 54, 93–9.
14. Pulver, A. E., Karayiorgou, M., Lasseter, V. K., Wolyniec, P., Kasch, L., Antonarakis, S., Housman, D., Kazazian, H. H., Meyers, D., Nestadt, G., Ott, J., Liang, K. -Y., Lamacz, M., Thomas, M., Childs, B., Diehl, S., Wang, S., Murphy, B., Sun, C. -e., O'Neill, A., Nie, L., Sham, P., Burke, J., Duke, B. W., Duke, F., Kipps, B. R., Bray, J., Hunt, W., Shinkwin, R., Nuallain, M. N., Su, Y., MacLean, C. J., Walsh, D., Kendler, K., Gill, M., Vallada, H., Mant, R., Asherson, P., Collier, D., Parfitt, E., Roberts, E., Nanko, S., Walsh, C., Daniels, J., Murray, R., McGuffin, P., Owen, M., Laurent, C., Dumas, J. -B., d'Amato, T., Jay, M., Martinez, M., Campion, D. & Mallet, J. (1994). Follow-up of a report of a potential linkage for schizophrenia on chromosome 22q12-q13.1: Part 2. Am. J. Med. Genetics 54, 44–50.
15. Pulver, A. E., Karayiorgou, M., Wolyniec, P. S., Lasseter, V. K., Kasch, L., Nestadt, G., Antonarakis, S., Housman, D., Kazazian, H. H., Meyers, D. & et al. (1994). Sequential strategy to identify a susceptibility gene for schizophrenia: report of potential linkage on chromosome 22q12-q13.1: Part 1. Am. J. Med. Genetics 54, 36–43.
16. Schwab, S. G., Lerer, B., Albus, M., Maier, W., Hallmayer, J., Fimmers, R., Lichtermann, D., Minges, J., Bondy, B., Ackenheil, M. & et al. (1995). Potential linkage for schizophrenia on chromosome 22q12-q13: a replication study. Am. J. Med. Genetics 60, 436–43.
17. Vallada, H. P., Gill, M., Sham, P., Lim, L. C., Nanko, S., Asherson, P., Murray, R. M., McGuffin, P., Owen, M. & Collier, D. (1995). Linkage studies on chromosome 22 in familial schizophrenia. Am. J. Med. Genetics 60, 139–46.
18. Wolf, S. S., Hyde, T. M. & Weinberger, D. R. (1993). Neurobiology of a schizophrenia. Curr. Opinion Neurol. Neurosurg. 6, 86–92.
19. Arnold, S. E., Lee, V. M., Gur, R. E. & Trojanowski, J. Q. (1991). Abnormal expression of two microtubule-associated proteins (MAP2 and MAP5) in specific subfields of the hippocampal formation in schizophrenia. Proc. Natl. Acad. Sci. USA 88, 10850–4.
20. Beckmann, H. & Jakob, H. (1991). Prenatal disturbances of nerve cell migration in the entorhinal region: a common vulnerability factor in functional psychoses? J. Neural Transmiss. 84, 155–64.
21. Conrad, A. J., Abebe, T., Austin, R., Forsythe, S. & Scheibel, A. B. (1991). Hippocampal pyramidal cell disarray in schizophrenia as a bilateral phenomenon. Arch. Gen. Psych. 48, 413–7.
22. Keshavan, M. S., Anderson, S. & Pettegrew, J. W. (1994). Is schizophrenia due to excessive synaptic pruning in the prefrontal cortex? The Feinberg hypothesis revisited. Journal of Psychiatric Research 28, 239–65.
23. Sambrook, J., Fritsch, E. F. & Maniatis, T. (1989). Molecular Cloning: A Laboratory Manual (2nd Edition) (Cold Spring Harbor, N.Y.: Cold Spring Harbor Laboratory Press).

What is claimed is:

1. An isolated and purified nucleic acid molecule which encodes an isoform of synapsin III, said isoform selected from the group consisting of the amino acid sequence comprising SEQ ID NO:1, the amino acid sequence comprising SEQ ID NO:6 and the amino acid sequence comprising SEQ ID NO:8.

2. The isolated and purified nucleic acid of claim 1, wherein the nucleic acid sequence is selected from the group consisting of the nucleic acid of SEQ ID NO:2, the nucleic acid of SEQ ID NO:5, and the nucleic acid of SEQ ID NO:7.

3. A recombinant virus comprising the isolated nucleic acid molecule in accordance with claim 2.

4. A vector comprising the nucleic acid sequence of either of claim 1 or 2.

5. The vector of claim 4 wherein the vector is a virus.

6. A unicellular host comprising the vector of claim 4.

7. A recombinant virus comprising the isolated nucleic acid molecule in accordance with claim 1.

8. The unicellular host of claim 6 wherein the unicellular host is selected from the group consisting of *E. coli*, Pseudomonas, Bacillus, Streptomyces, yeasts, CHO, R1.1, B-W, L-M, COS 1, COS 7, BSC1, BSC40, and BMT10 cells, plant cells, insect cells, and human cells in tissue culture.

* * * * *

SEQUENCE LISTING

<160> NUMBER OF SEQ ID NOS: 8

<210> SEQ ID NO 1
<211> LENGTH: 580
<212> TYPE: PRT
<213> ORGANISM: Homo sapiens
<220> FEATURE:
<221> NAME/KEY: unsure
<222> LOCATION: (430)
<223> OTHER INFORMATION: Xaa can be any amino acid

<400> SEQUENCE: 1

Met Asn Phe Leu Arg Arg Arg Leu Ser Asp Ser Ser Phe Met Ala Asn
 1               5                  10                  15

```
Leu Pro Asn Gly Tyr Met Thr Asp Leu Gln Arg Pro Asp Ser Ser Thr
             20                  25                  30

Ser Ser Pro Ala Ser Pro Ala Met Glu Arg Arg His Pro Gln Pro Leu
         35                  40                  45

Ala Ala Ser Phe Ser Ser Pro Gly Ser Ser Leu Phe Ser Ser Leu Ser
     50                  55                  60

Ser Ala Met Lys Gln Ala Pro Gln Ala Thr Ser Gly Leu Met Glu Pro
 65                  70                  75                  80

Pro Gly Pro Ser Thr Pro Ile Val Gln Arg Pro Arg Ile Leu Leu Val
                 85                  90                  95

Ile Asp Asp Ala His Thr Asp Trp Ser Lys Tyr Phe His Gly Lys Lys
                100                 105                 110

Val Asn Gly Glu Ile Glu Ile Arg Val Glu Gln Ala Glu Phe Ser Glu
            115                 120                 125

Leu Asn Leu Ala Ala Tyr Val Thr Gly Gly Cys Met Val Asp Met Gln
        130                 135                 140

Val Val Arg Asn Gly Thr Lys Val Val Ser Arg Ser Phe Lys Pro Asp
145                 150                 155                 160

Phe Ile Leu Val Arg Gln His Ala Tyr Ser Met Ala Leu Gly Glu Asp
                165                 170                 175

Tyr Arg Ser Leu Val Ile Gly Leu Gln Tyr Gly Gly Leu Pro Ala Val
            180                 185                 190

Asn Ser Leu Tyr Ser Val Tyr Asn Phe Cys Ser Lys Pro Trp Val Phe
        195                 200                 205

Ser Gln Leu Ile Lys Ile Phe His Ser Leu Gly Pro Glu Lys Phe Pro
210                 215                 220

Leu Val Glu Gln Thr Phe Phe Pro Asn His Lys Pro Met Val Thr Ala
225                 230                 235                 240

Pro His Phe Pro Val Val Lys Leu Gly His Ala His Ala Gly Met
                245                 250                 255

Gly Lys Ile Lys Val Glu Asn Gln Leu Asp Phe Gln Asp Ile Thr Ser
            260                 265                 270

Val Val Ala Met Ala Lys Thr Tyr Ala Thr Thr Glu Ala Phe Ile Asp
        275                 280                 285

Ser Lys Tyr Asp Ile Arg Ile Gln Lys Ile Gly Ser Asn Tyr Lys Ala
290                 295                 300

Tyr Met Arg Thr Ser Ile Ser Gly Asn Trp Lys Ala Asn Thr Gly Ser
305                 310                 315                 320

Ala Met Leu Glu Gln Val Ala Met Thr Glu Arg Tyr Arg Leu Trp Val
                325                 330                 335

Asp Ser Cys Ser Glu Met Phe Gly Gly Leu Asp Ile Cys Ala Val Lys
            340                 345                 350

Ala Val His Ser Lys Asp Gly Arg Asp Tyr Ile Ile Glu Val Met Asp
        355                 360                 365

Ser Ser Met Pro Leu Ile Gly Glu His Val Glu Glu Asp Arg Gln Leu
370                 375                 380

Met Ala Asp Leu Val Val Ser Lys Met Ser Gln Leu Pro Met Pro Gly
385                 390                 395                 400

Gly Thr Ala Pro Ser Pro Leu Arg Pro Trp Ala Pro Gln Ile Lys Ser
                405                 410                 415

Ala Lys Ser Pro Gly Gln Ala Gln Leu Gly Pro Gln Leu Xaa Gln Pro
            420                 425                 430
```

```
Gln Pro Arg Pro Pro Gln Gly Gly Pro Arg Gln Ala Gln Ser Pro
        435                 440                 445
Gln Pro Gln Arg Ser Gly Ser Pro Ser Gln Gln Arg Leu Ser Pro Gln
    450                 455                 460
Gly Gln Gln Pro Leu Ser Pro Gln Ser Gly Ser Pro Gln Gln Gln Arg
465                 470                 475                 480
Ser Pro Gly Ser Pro Gln Leu Ser Arg Ala Ser Ser Gly Ser Ser Pro
                485                 490                 495
Asn Gln Ala Ser Lys Pro Gly Ala Thr Leu Ala Ser Gln Pro Arg Pro
                500                 505                 510
Pro Val Gln Gly Arg Ser Thr Ser Gln Gln Gly Glu Glu Ser Lys Lys
            515                 520                 525
Pro Ala Pro Pro His Pro His Leu Asn Lys Ser Gln Ser Leu Thr Asn
        530                 535                 540
Ser Leu Ser Thr Ser Asp Thr Ser Gln Arg Gly Thr Pro Ser Glu Asp
545                 550                 555                 560
Glu Ala Lys Ala Glu Thr Ile Arg Asn Leu Arg Lys Ser Phe Ala Ser
                565                 570                 575
Leu Phe Ser Asp
        580

<210> SEQ ID NO 2
<211> LENGTH: 2265
<212> TYPE: DNA
<213> ORGANISM: Homo sapiens
<220> FEATURE:
<221> NAME/KEY: unsure
<222> LOCATION: (2156)
<223> OTHER INFORMATION: N can be A,T,C, or G

<400> SEQUENCE: 2
tgggtaggag ccagtcatct ccatccatcc acagccatga atttcctccg gcgacgtctc      60
tctgacagca gcttcatggc caacctgcct aatggctata tgacggacct gcaacgccca     120
gatagctcca ccagctcacc tgcttccccc gccatggaga ggaggcaccc ccagcccctg     180
gctgcctcct tctcctctcc aggatccagc cttttagct ccctctccag tgccatgaag      240
caggcccctc aggccacctc aggactgatg gagcctccag gtccctccac gcccattgtt     300
caaagaccca ggatcctgtt ggtgatcgat gatgcccata cagactggtc gaagtatttc     360
catgggaaga aggtgaatgg agagattgag atccgagtgg agcaggctga attctcagag     420
ttgaacctag ctgcctatgt gaccgggggc tgcatggtgg acatgcaggt cgtgagaaat     480
gggaccaaag tggtgagcag atccttcaag ccagacttca tcctggtccg ccagcatgcc     540
tacagcatgg ccctggggga agactaccgc agcctggtca tcggcctgca gtatggaggg     600
ctgcctgctg tcaactctct ctactccgtc tacaacttct gcagcaagcc ctgggtgttc     660
tctcagctca ttaagatctt ccattccctg gtcctgaga agttcccgct tgtggagcaa     720
acatttttcc ccaaccataa gccaatggtc acagccccac acttcccggt ggtagtcaag     780
ctgggacatg cccacgctgg aatgggaaag atcaaagtgg aaaaccagct tgacttccag     840
gacatcacca gcgtggtcgc catggccaaa acatacgcca ccaccgaggc gttcatcgac     900
tccaagtacg acatccgcat ccagaaaatt ggatccaact caaggctta catgagaacc     960 tccatctctg ggaactggaa ggccaacaca ggctctgcca tgctggagca ggtggccatg    1020
acagagaggt acaggctgtg ggtggacagc tgctcggaaa tgtttggcgg cctggacatc    1080
tgtgccgtca aggctgtcca cagcaaggat ggcagagatt acatcatcga ggtaatggac    1140
```

-continued

```
agctcaatgc cgctgattgg agagcatgtg gaagaggaca gacagctgat ggccgacctt    1200
gttgtctcca aaatgagcca gctcccgatg ccaggaggca cagcgccctc ccccctcaga    1260
ccttgggctc cacagattaa atcagcgaaa tccccagggc aagcccagct ggggcctcag    1320
ctargccagc cccagccacg cccacctccg caaggaggcc ctcgccaagc tcagtctcct    1380
cagccccaga gatctggaag cccctcccaa cagaggctct ccccacaagg ccagcagccc    1440
ctgagccccc agtccggatc tccacagcag caaaggtcac caggctctcc gcagctatcc    1500
cgggcatcca gtggcagctc cccaaaccar gcctccaagc caggtgccac cctcgcctca    1560
cagccccggc ccctgtgcag ggccgtagt acctcccagc agggtgaaga gtccaagaag    1620
ccagcaccac cccatccgca tctcaacaaa tctcagtccc tgactaacag cctcagcaca    1680
tccgacacct cccagcgtgg accccaagt gaagacgagg ccaaggctga aaccatccgc    1740
aacctgagga agtcttttgc cagcctgttc tctgactaac gccatccagg ctgggagggg    1800
aagagtgcta tggtacactc gtccccytcc tgcctcatct tccttctcag ccttggttcc    1860
tgatgggaac agaatggagg gcctgagaac atactttcta aatgcctttg acccaggaac    1920
cgattatcta tatttgttcc catttccctt caccgtgaca ttccagcatt gtctgactgt    1980
gaggtgggcc tttgagagcc tccaggttcc tcaaaacagg cctgagcgat gggcatcaca    2040
ccctctgcct acccacgtgc atgcttacct gccagataac caagtgagat gtctgcgagt    2100
ggctagtttt cacattctta ctagtgtttg gctcaccttt gggcaaaggc cccytntagg    2160
ccttgcccca cctccatcaa acgcagacac tgtagtcaga cctcagcaat ataggaggca    2220
ataatctttt aacagtgttt tgcaaacaaa caaaaaaaaa aaaaa                    2265
```

<210> SEQ ID NO 3
<211> LENGTH: 582
<212> TYPE: PRT
<213> ORGANISM: Homo sapiens

<400> SEQUENCE: 3

```
Met Met Asn Phe Leu Arg Arg Arg Leu Ser Asp Ser Ser Phe Ile Ala
  1               5                  10                  15

Asn Leu Pro Asn Gly Tyr Met Thr Asp Leu Gln Arg Pro Glu Pro Gln
             20                  25                  30

Gln Pro Pro Pro Pro Pro Gly Pro Gly Ala Ala Ser Ala Ser
         35                  40                  45

Ala Ala Pro Pro Thr Ala Ser Pro Gly Pro Glu Arg Arg Pro Pro
     50                  55                  60

Ala Ser Ala Pro Ala Ala Gln Pro Ala Pro Thr Pro Ser Val Gly Ser
 65                  70                  75                  80

Ser Phe Phe Ser Ser Leu Ser Gln Ala Val Lys Gln Thr Ala Ala Ser
                 85                  90                  95

Ala Gly Leu Val Asp Ala Pro Ala Pro Ala Pro Ala Ala Ala Arg Lys
            100                 105                 110

Ala Lys Val Leu Leu Val Val Asp Glu Pro His Ala Asp Trp Ala Lys
        115                 120                 125

Cys Phe Arg Gly Lys Lys Val Leu Gly Asp Tyr Asp Ile Lys Val Glu
    130                 135                 140

Gln Ala Glu Phe Ser Glu Leu Asn Leu Val Ala His Ala Asp Gly Thr
145                 150                 155                 160

Tyr Ala Val Asp Met Gln Val Leu Arg Asn Gly Thr Lys Val Arg
                165                 170                 175
```

```
Ser Phe Arg Pro Asp Phe Val Leu Ile Arg Gln His Ala Phe Gly Met
            180                 185                 190

Ala Glu Asn Glu Asp Phe Arg His Leu Ile Ile Gly Met Gln Tyr Ala
        195                 200                 205

Gly Leu Pro Ser Ile Asn Ser Leu Glu Ser Ile Tyr Asn Phe Cys Asp
        210                 215                 220

Lys Pro Trp Val Phe Ala Gln Leu Val Ala Ile Tyr Lys Thr Leu Gly
225                 230                 235                 240

Gly Glu Lys Phe Pro Leu Ile Glu Gln Thr Tyr Tyr Pro Asn His Lys
            245                 250                 255

Glu Met Leu Thr Leu Pro Thr Phe Pro Val Val Lys Ile Gly His
            260                 265                 270

Ala His Ser Gly Met Gly Lys Val Lys Val Glu Asn His Tyr Asp Phe
            275                 280                 285

Gln Asp Ile Ala Ser Val Val Ala Leu Thr Gln Thr Tyr Ala Thr Ala
        290                 295                 300

Glu Pro Phe Ile Asp Ser Lys Tyr Asp Ile Arg Val Gln Lys Ile Gly
305                 310                 315                 320

Asn Asn Tyr Lys Ala Tyr Met Arg Thr Ser Ile Ser Gly Asn Trp Lys
            325                 330                 335

Thr Asn Thr Gly Ser Ala Met Leu Glu Gln Ile Ala Met Ser Asp Arg
            340                 345                 350

Tyr Lys Leu Trp Val Asp Thr Cys Ser Glu Met Phe Gly Gly Leu Asp
            355                 360                 365

Ile Cys Ala Val Lys Ala Val His Gly Lys Asp Gly Lys Asp Tyr Ile
            370                 375                 380

Phe Glu Val Met Asp Cys Ser Met Pro Leu Ile Gly Glu His Gln Val
385                 390                 395                 400

Glu Asp Arg Gln Leu Ile Thr Glu Leu Val Ile Ser Lys Met Asn Gln
                405                 410                 415

Leu Leu Ser Arg Thr Pro Ala Leu Ser Pro Gln Arg Pro Leu Thr Thr
            420                 425                 430

Gln Gln Pro Gln Ser Gly Thr Leu Lys Asp Pro Asp Ser Ser Lys Thr
            435                 440                 445

Pro Pro Gln Arg Pro Pro Gln Gly Gly Pro Gly Gln Pro Gln Gly
            450                 455                 460

Met Gln Pro Pro Gly Lys Val Leu Pro Pro Arg Arg Leu Pro Pro Gly
465                 470                 475                 480

Pro Ser Leu Pro Pro Ser Ser Ser Ser Ser Ser Ser Ser Ser Ser Ser
            485                 490                 495

Ala Pro Gln Arg Pro Gly Gly Pro Thr Thr His Gly Asp Ala Pro Ser
            500                 505                 510

Ser Ser Ser Ser Leu Ala Glu Ala Gln Pro Pro Leu Ala Ala Pro Pro
            515                 520                 525

Gln Lys Pro Gln Pro His Pro Gln Leu Asn Lys Ser Gln Ser Leu Thr
            530                 535                 540

Asn Ala Phe Ser Phe Ser Glu Ser Ser Phe Phe Arg Ser Ser Ala Asn
545                 550                 555                 560

Glu Asp Glu Ala Lys Ala Glu Thr Ile Arg Ser Leu Arg Lys Ser Phe
            565                 570                 575

Ala Ser Leu Phe Ser Asp
            580
```

<210> SEQ ID NO 4
<211> LENGTH: 696
<212> TYPE: PRT
<213> ORGANISM: Homo sapiens

<400> SEQUENCE: 4

```
Met Asn Tyr Leu Arg Arg Leu Ser Asp Ser Asn Phe Met Ala Asn
 1               5                  10                  15

Leu Pro Asn Gly Tyr Met Thr Asp Leu Gln Arg Pro Gln Pro Pro
                20                  25                  30

Pro Pro Pro Gly Ala His Ser Pro Gly Ala Thr Pro Gly Pro Gly Thr
            35                  40                  45

Ala Thr Ala Glu Arg Ser Ser Gly Val Ala Pro Ala Ala Ser Pro Ala
        50                  55                  60

Ala Pro Ser Pro Gly Ser Ser Gly Gly Gly Phe Phe Ser Ser Leu
 65                  70                  75                  80

Ser Asn Ala Val Lys Gln Thr Ala Ala Ala Ala Thr Phe Ser
                85                  90                  95

Glu Gln Val Gly Gly Ser Gly Ala Gly Arg Gly Gly Ala Ala
                100                 105                 110

Ser Arg Val Leu Leu Val Ile Asp Glu Pro His Thr Asp Trp Ala Lys
        115                 120                 125

Tyr Phe Lys Gly Lys Lys Ile His Gly Glu Ile Asp Ile Lys Val Glu
    130                 135                 140

Gln Ala Glu Phe Ser Asp Leu Asn Leu Val Ala His Ala Asn Gly Gly
145                 150                 155                 160

Phe Ser Val Asp Met Glu Val Leu Arg Asn Gly Val Lys Val Val Arg
                165                 170                 175

Ser Leu Lys Pro Asp Phe Val Leu Ile Arg Gln His Ala Phe Ser Met
                180                 185                 190

Ala Arg Asn Gly Asp Tyr Arg Ser Leu Val Ile Gly Leu Gln Tyr Ala
        195                 200                 205

Gly Ile Pro Ser Val Asn Ser Leu His Ser Val Tyr Asn Phe Cys Asp
    210                 215                 220

Lys Pro Trp Val Phe Ala Gln Met Val Arg Leu His Lys Lys Leu Gly
225                 230                 235                 240

Thr Glu Glu Phe Pro Leu Ile Asp Gln Thr Phe Tyr Pro Asn His Lys
                245                 250                 255

Glu Met Leu Ser Ser Thr Thr Tyr Pro Val Val Lys Met Gly His
                260                 265                 270

Ala His Ser Gly Met Gly Lys Val Lys Val Asp Asn Gln His Asp Phe
        275                 280                 285

Gln Asp Ile Ala Ser Val Val Ala Leu Thr Lys Thr Tyr Ala Thr Ala
    290                 295                 300

Glu Pro Phe Ile Asp Ala Lys Tyr Asp Val Arg Val Gln Lys Ile Gly
305                 310                 315                 320

Gln Asn Tyr Lys Ala Tyr Met Arg Thr Ser Val Ser Gly Asn Trp Lys
                325                 330                 335

Thr Asn Thr Gly Ser Ala Met Leu Glu Gln Ile Ala Met Ser Asp Arg
                340                 345                 350

Tyr Lys Leu Trp Val Asp Thr Cys Ser Glu Ile Phe Gly Gly Leu Asp
        355                 360                 365

Ile Cys Ala Val Glu Ala Leu His Gly Lys Asp Gly Arg Asp His Ile
    370                 375                 380
```

```
Ile Glu Val Val Gly Ser Ser Met Pro Leu Ile Gly Asp His Gln Asp
385                 390                 395                 400

Glu Asp Lys Gln Leu Ile Val Glu Leu Val Asn Lys Met Ala Gln
            405                 410                 415

Ala Leu Pro Arg Gln Arg Gln Arg Asp Ala Ser Pro Gly Arg Gly Ser
            420                 425                 430

His Gly Gln Thr Pro Ser Pro Gly Ala Leu Pro Leu Gly Arg Gln Thr
            435                 440                 445

Ser Gln Gln Pro Ala Gly Pro Ala Gln Gln Glu Pro Pro Gln
    450                 455                 460

Gly Gly Pro Pro Gln Pro Gly Pro Gly Pro Arg Gln Gly Pro Pro
465                 470                 475                 480

Leu Gln Gln Arg Pro Pro Gln Gly Gln Gln His Leu Ser Gly Leu
                485                 490                 495

Gly Pro Pro Ala Gly Ser Pro Leu Pro Gln Arg Leu Pro Ser Pro Thr
            500                 505                 510

Ser Ala Pro Gln Gln Pro Ala Ser Gln Ala Ala Pro Pro Thr Gln Gly
            515                 520                 525

Gln Gly Arg Gln Ser Arg Pro Val Ala Gly Gly Pro Gly Ala Pro Pro
    530                 535                 540

Ala Ala Arg Pro Pro Ala Ser Pro Ser Pro Gln Arg Gln Ala Gly Pro
545                 550                 555                 560

Pro Gln Ala Thr Arg Gln Thr Ser Val Ser Gly Pro Ala Pro Pro Lys
                565                 570                 575

Ala Ser Gly Ala Pro Pro Gly Gly Gln Gln Arg Gln Gly Pro Pro Gln
            580                 585                 590

Lys Pro Pro Gly Pro Ala Gly Pro Thr Arg Gln Ala Ser Gln Ala Gly
            595                 600                 605

Pro Val Pro Arg Thr Gly Pro Pro Thr Thr Gln Pro Arg Pro Ser
    610                 615                 620

Gly Pro Gly Pro Ala Gly Ala Pro Lys Pro Gln Leu Ala Gln Lys Pro
625                 630                 635                 640

Ser Gln Asp Val Pro Pro Ala Thr Ala Ala Gly Gly Pro Pro
                645                 650                 655

His Pro Gln Leu Phe Asn Leu Pro Glu Pro Ala Pro Pro Arg Pro Ser
            660                 665                 670

Leu Ser Gln Asp Glu Val Lys Ala Glu Thr Ile Arg Ser Leu Arg Lys
            675                 680                 685

Ser Phe Ala Ser Leu Phe Ser Asp
    690                 695

<210> SEQ ID NO 5
<211> LENGTH: 2065
<212> TYPE: DNA
<213> ORGANISM: Homo sapiens

<400> SEQUENCE: 5
tgggtaggag ccagtcatct ccatccatcc acagccatga atttcctccg gcgacgtctc     60
tctgacagca gcttcatggc caacctgcct aatggctata tgacggacct gcaacgccca    120
gatagctcca ccagctcacc tgcttccccc gccatggaga ggaggcaccc ccagcccctg    180
gctgcctcct ctcctctcc aggatccagc ctttttagct ccctctccag tgccatgaag    240
caggcccctc aggccaccte aggactgatg gagcctccag gtccctccac gcccattgtt    300
```

-continued

```
caaagaccca ggatcctgtt ggtgatcgat gatgcccata cagactggtc gaagtatttc    360 catggaaga aggtgaatgg agagattgag atccgagtgg agcaggctga attctcagag     420
ttgaacctag ctgcctatgt gaccgggggc tgcatggtgg acatgcaggt cgtgagaaat    480
gggaccaaag tggtgagcag atccttcaag ccagacttca tcctggtccg ccagcatgcc    540
tacagcatgg ccctggggga agactaccgc agcctggtca tcggcctgca gtatggaggg    600
ctgcctgctg tcaactctct ctactccgtc tacaacttct gcagcaagcc ctgggtgttc    660
tctcagctca ttaagatctt ccattccctg ggtcctgaga agttcccgct gtgtgagcaa    720 acattttttcc ccaaccataa gccaatggtc acagccccac acttcccggt ggtagtcaag    780
ctgggacatg cccacgctgg aatgggaaag atcaaagtgg aaaaccagct tgacttccag    840
gacatcacca gcgtggtcgc catggccaaa acatacgcca ccaccgaggc gttcatcgac    900
tccaagtacg acatccgcat ccagaaaatt ggatccaact acaaggctta catgagaacc    960
tccatctctg ggaactggaa ggccaacaca ggctctgcca tgctggagca ggtggccatg   1020
acagagaggt acaggctgtg ggtggacagc tgctcggaaa tgtttggcgg cctggacatc   1080
tgtgccgtca aggctgtcca cagcaaggat ggcagagatt acatcatcga ggtaatggac   1140
agctcaatgc cgctgattgg agagcatgtg aagaggaca gacagctgat ggccgacctt   1200
gttgtctcca aaatgagcca gctcccgatg ccaggaggca cagcgccctc cccctcaga    1260 ccttgggagg ccctcgccaa gctcagtctc ctcagcccca gagatctgga agccctccc   1320 aacagaggct ctccccacaa ggccagcagc ccctgagccc ccagtccgga tctccacagc   1380
agcaaaggtc accaggctct ccgcagctat cccgggcatc cagtggcagc tccccaaacc   1440
aggcctccaa gccaggtgcc accctcgcct cacagccccg gccccctgtg cagggccgta   1500
gtacctccca gcagggtgaa gagtccaaga agccagcacc accccatccg catctcaaca   1560
aatctcagtc cctgactaac agcctcagca catccgacac ctcccagcgt gggaccccaa   1620
gtgaagacga ggccaaggct gaaaccatcc gcaacctgag gaagtctttt gccagcctgt   1680
tctctgacta acgccatcca ggctgggagg ggaagagtgc tatggtacac tcgtcccct    1740 cctgcctcat cttccttctc agccttggtt cctgatggga acagaatgga gggcctgaga   1800
acatactttc taaatgcctt tgacccagga accgattatc tatatttgtt cccatttttcc   1860 ttcaccgtga cattccagca ttgtctgact gtgaggtggg cctttgagag cctccaggtt   1920
cctcaaaaca ggcctgagcg atgggcatca cacccctctgc ctacccacgt gcatgcttac   1980
ctgccagata accaagtgag atgtctgcga gtggctagtt ttcacattct tactagtgtt   2040
tggctcacct ttgggcaaag gcccc                                          2065
```

<210> SEQ ID NO 6
<211> LENGTH: 439
<212> TYPE: PRT
<213> ORGANISM: Homo sapiens

<400> SEQUENCE: 6

```
Met Asn Phe Leu Arg Arg Arg Leu Ser Asp Ser Ser Phe Met Ala Asn
 1               5                  10                  15

Leu Pro Asn Gly Tyr Met Thr Asp Leu Gln Arg Pro Asp Ser Ser Thr
             20                  25                  30

Ser Ser Pro Ala Ser Pro Ala Met Glu Arg Arg His Pro Gln Pro Leu
         35                  40                  45

Ala Ala Ser Phe Ser Ser Pro Gly Ser Ser Leu Phe Ser Ser Leu Ser
     50                  55                  60
```

-continued

Ser Ala Met Lys Gln Ala Pro Gln Ala Thr Ser Gly Leu Met Glu Pro
 65                  70                  75                  80

Pro Gly Pro Ser Thr Pro Ile Val Gln Arg Pro Arg Ile Leu Leu Val
                 85                  90                  95

Ile Asp Asp Ala His Thr Asp Trp Ser Lys Tyr Phe His Gly Lys Lys
            100                 105                 110

Val Asn Gly Glu Ile Glu Ile Arg Val Glu Gln Ala Glu Phe Ser Glu
        115                 120                 125

Leu Asn Leu Ala Ala Tyr Val Thr Gly Gly Cys Met Val Asp Met Gln
    130                 135                 140

Val Val Arg Asn Gly Thr Lys Val Val Ser Arg Ser Phe Lys Pro Asp
145                 150                 155                 160

Phe Ile Leu Val Arg Gln His Ala Tyr Ser Met Ala Leu Gly Glu Asp
                165                 170                 175

Tyr Arg Ser Leu Val Ile Gly Leu Gln Tyr Gly Gly Leu Pro Ala Val
            180                 185                 190

Asn Ser Leu Tyr Ser Val Tyr Asn Phe Cys Ser Lys Pro Trp Val Phe
        195                 200                 205

Ser Gln Leu Ile Lys Ile Phe His Ser Leu Gly Pro Glu Lys Phe Pro
    210                 215                 220

Leu Val Glu Gln Thr Phe Phe Pro Asn His Lys Pro Met Val Thr Ala
225                 230                 235                 240

Pro His Phe Pro Val Val Lys Leu Gly His Ala His Ala Gly Met
                245                 250                 255

Gly Lys Ile Lys Val Glu Asn Gln Leu Asp Phe Gln Asp Ile Thr Ser
            260                 265                 270

Val Val Ala Met Ala Lys Thr Tyr Ala Thr Thr Glu Ala Phe Ile Asp
        275                 280                 285

Ser Lys Tyr Asp Ile Arg Ile Gln Lys Ile Gly Ser Asn Tyr Lys Ala
    290                 295                 300

Tyr Met Arg Thr Ser Ile Ser Gly Asn Trp Lys Ala Asn Thr Gly Ser
305                 310                 315                 320

Ala Met Leu Glu Gln Val Ala Met Thr Glu Arg Tyr Arg Leu Trp Val
                325                 330                 335

Asp Ser Cys Ser Glu Met Phe Gly Gly Leu Asp Ile Cys Ala Val Lys
            340                 345                 350

Ala Val His Ser Lys Asp Gly Arg Asp Tyr Ile Ile Glu Val Met Asp
        355                 360                 365

Ser Ser Met Pro Leu Ile Gly Glu His Val Glu Glu Asp Arg Gln Leu
    370                 375                 380

Met Ala Asp Leu Val Val Ser Lys Met Ser Gln Leu Pro Met Pro Gly
385                 390                 395                 400

Gly Thr Ala Pro Ser Pro Leu Arg Pro Trp Glu Ala Leu Ala Lys Leu
                405                 410                 415

Ser Leu Leu Ser Pro Arg Asp Leu Glu Ala Pro Asn Arg Gly Ser
            420                 425                 430

Pro His Lys Ala Ser Ser Pro
            435

<210> SEQ ID NO 7
<211> LENGTH: 1861
<212> TYPE: DNA
<213> ORGANISM: Homo sapiens

```
<400> SEQUENCE: 7
tgggtaggag ccagtcatct ccatccatcc acagccatga atttcctccg gcgacgtctc      60
tctgacagca gcttcatggc caacctgcct aatggctata tgacggacct gcaacgccca     120
gatagctcca ccagctcacc tgcttccccc gccatggaga ggaggcaccc ccagcccctg     180
gctgcctcct ctcctctcc aggatccagc cttttagct ccctctccag tgccatgaag       240
caggcccctc aggccacctc aggactgatg gagcctccag gtccctccac gcccattgtt     300
caaagaccca ggatcctgtt ggtgatcgat gatgcccata cagactggtc gaagtatttc     360
catgggaaga aggtgaatgg agagattgag atccgagtgg agcaggctga attctcagag     420
ttgaacctag ctgcctatgt gaccgggggc tgcatggtgg acatgcaggt cgtgagaaat     480
gggaccaaag tggtgagcag atccttcaag ccagacttca tcctggtccg ccagcatgcc     540
tacagcatgg ccctggggga agactaccgc agcctggtca tcggcctgca gtatggaggg     600
ctgcctgctg tcaactctct ctactccgtc tacaacttct gcagcaagcc ctgggtgttc     660
tctcagctca ttaagatctt ccattccctg ggtcctgaga gttcccgct tgtggagcaa      720
acatttttcc ccaaccataa gccaatggtc acagccccac acttcccggt ggtagtcaag     780
ctgggacatg cccacgctgg aatgggaaag atcaaagtgg aaaaccagct tgacttccag     840
gacatcacca gcgtggtcgc catggccaaa acatacgcca ccaccgaggc gttcatcgac     900
tccaagtacg acatccgcat ccagaaaatt ggatccaact acaaggctta catgagaacc     960
tccatctctg ggaactggaa ggccaacaca ggctctgcca tgctggagca ggtggccatg    1020
acagagaggt acaggctgtg ggtggacagc tgctcggaaa tgtttggcgg cctggacatc    1080
tgtgccgtca aggctgtcca cagcaaggat ggcagagatt acatcatcga ggtaatggac    1140
agctcaatgc cgctgattgg agagcatgtg aagaggaca gacagctgat ggccgacctt     1200
gttgtctcca aaatgagcca gctcccgatg ccaggaggca gcgccctc ccccctcaga      1260
ccttgggctc cacagattaa atcagcgaaa tccccagggc aagcccagct ggggcctcag    1320
ctaggccagc cccagccacg cccacctccg caagcaaatc tcagtccctg actaacagcc    1380
tcagcacatc cgacacctcc cagcgtggga ccccaagtga agacgaggcc aaggctgaaa    1440
ccatccgcaa cctgaggaag tcttttgcca gcctgttctc tgactaacgc catccaggct    1500
gggaggggaa gagtgctatg gtacactcgt cccctcctg cctcatcttc cttctcagcc     1560
ttggttcctg atgggaacag aatggagggc ctgagaacat actttctaaa tgcctttgac    1620
ccaggaaccg attatctata tttgttccca ttttccttca ccgtgacatt ccagcattgt    1680
ctgactgtga ggtgggcctt tgagagcctc caggttcctc aaaacaggcc tgagcgatgg    1740
gcatcacacc ctctgcctac ccacgtgcat gcttacctgc cagataacca agtgagatgt    1800
ctgcgagtgg ctagttttca cattcttact agtgtttggc tcacctttgg gcaaaggccc    1860
c                                                                    1861

<210> SEQ ID NO 8
<211> LENGTH: 444
<212> TYPE: PRT
<213> ORGANISM: Homo sapiens

<400> SEQUENCE: 8

Met Asn Phe Leu Arg Arg Arg Leu Ser Asp Ser Ser Phe Met Ala Asn
  1               5                  10                  15

Leu Pro Asn Gly Tyr Met Thr Asp Leu Gln Arg Pro Asp Ser Ser Thr
                 20                  25                  30
```

```
Ser Ser Pro Ala Ser Pro Ala Met Glu Arg Arg His Pro Gln Pro Leu
        35                  40                  45
Ala Ala Ser Phe Ser Ser Pro Gly Ser Ser Leu Phe Ser Ser Leu Ser
        50                  55                  60
Ser Ala Met Lys Gln Ala Pro Gln Ala Thr Ser Gly Leu Met Glu Pro
 65                  70                  75                  80
Pro Gly Pro Ser Thr Pro Ile Val Gln Arg Pro Arg Ile Leu Leu Val
                     85                  90                  95
Ile Asp Asp Ala His Thr Asp Trp Ser Lys Tyr Phe His Gly Lys Lys
            100                 105                 110
Val Asn Gly Glu Ile Glu Ile Arg Val Glu Gln Ala Glu Phe Ser Glu
        115                 120                 125
Leu Asn Leu Ala Ala Tyr Val Thr Gly Gly Cys Met Val Asp Met Gln
    130                 135                 140
Val Val Arg Asn Gly Thr Lys Val Val Ser Arg Ser Phe Lys Pro Asp
145                 150                 155                 160
Phe Ile Leu Val Arg Gln His Ala Tyr Ser Met Ala Leu Gly Glu Asp
                165                 170                 175
Tyr Arg Ser Leu Val Ile Gly Leu Gln Tyr Gly Gly Leu Pro Ala Val
            180                 185                 190
Asn Ser Leu Tyr Ser Val Tyr Asn Phe Cys Ser Lys Pro Trp Val Phe
        195                 200                 205
Ser Gln Leu Ile Lys Ile Phe His Ser Leu Gly Pro Glu Lys Phe Pro
    210                 215                 220
Leu Val Glu Gln Thr Phe Phe Pro Asn His Lys Pro Met Val Thr Ala
225                 230                 235                 240
Pro His Phe Pro Val Val Lys Leu Gly His Ala His Ala Gly Met
                245                 250                 255
Gly Lys Ile Lys Val Glu Asn Gln Leu Asp Phe Gln Asp Ile Thr Ser
            260                 265                 270
Val Val Ala Met Ala Lys Thr Tyr Ala Thr Thr Glu Ala Phe Ile Asp
        275                 280                 285
Ser Lys Tyr Asp Ile Arg Ile Gln Lys Ile Gly Ser Asn Tyr Lys Ala
    290                 295                 300
Tyr Met Arg Thr Ser Ile Ser Gly Asn Trp Lys Ala Asn Thr Gly Ser
305                 310                 315                 320
Ala Met Leu Glu Gln Val Ala Met Thr Glu Arg Tyr Arg Leu Trp Val
                325                 330                 335
Asp Ser Cys Ser Glu Met Phe Gly Gly Leu Asp Ile Cys Ala Val Lys
            340                 345                 350
Ala Val His Ser Lys Asp Gly Arg Asp Tyr Ile Ile Glu Val Met Asp
        355                 360                 365
Ser Ser Met Pro Leu Ile Gly Glu His Val Glu Glu Asp Arg Gln Leu
    370                 375                 380
Met Ala Asp Leu Val Val Ser Lys Met Ser Gln Leu Pro Met Pro Gly
385                 390                 395                 400
Gly Thr Ala Pro Ser Pro Leu Arg Pro Trp Ala Pro Gln Ile Lys Ser
                405                 410                 415
Ala Lys Ser Pro Gly Gln Ala Gln Leu Gly Pro Gln Leu Gly Gln Pro
            420                 425                 430
Gln Pro Arg Pro Pro Gln Ala Asn Leu Ser Pro
        435                 440
```